United States Patent
Yamada et al.

(10) Patent No.: US 9,249,135 B2
(45) Date of Patent: Feb. 2, 2016

(54) THERAPEUTIC AGENT FOR MOOD DISORDERS

(75) Inventors: Koji Yamada, Shizuoka (JP); Tomoyuki Kanda, Shizuoka (JP)

(73) Assignee: KYOWA HAKKO KIRIN CO., LTD., Tokyo (JP)

(*) Notice: Subject to any disclaimer, the term of this patent is extended or adjusted under 35 U.S.C. 154(b) by 293 days.

(21) Appl. No.: 13/393,035

(22) PCT Filed: Sep. 2, 2010

(86) PCT No.: PCT/JP2010/064988
§ 371 (c)(1),
(2), (4) Date: Mar. 20, 2012

(87) PCT Pub. No.: WO2011/027805
PCT Pub. Date: Mar. 10, 2011

(65) Prior Publication Data
US 2012/0184554 A1 Jul. 19, 2012

(30) Foreign Application Priority Data
Sep. 2, 2009 (JP) ................. 2009-202893

(51) Int. Cl.
*A61K 31/34* (2006.01)
*A61K 31/35* (2006.01)
*A61K 31/426* (2006.01)
*A61K 31/435* (2006.01)
*C07D 417/14* (2006.01)
*A61K 31/4439* (2006.01)
*A61K 31/506* (2006.01)
*A61K 31/5377* (2006.01)
*C07D 491/048* (2006.01)
*C07D 491/052* (2006.01)
*C07D 495/04* (2006.01)

(52) U.S. Cl.
CPC .............. *C07D 417/14* (2013.01); *A61K 31/34* (2013.01); *A61K 31/35* (2013.01); *A61K 31/426* (2013.01); *A61K 31/435* (2013.01); *A61K 31/4439* (2013.01); *A61K 31/506* (2013.01); *A61K 31/5377* (2013.01); *C07D 491/048* (2013.01); *C07D 491/052* (2013.01); *C07D 495/04* (2013.01)

(58) Field of Classification Search
CPC ..... A61K 31/34; A61K 31/35; A61K 31/426; A61K 31/435
USPC .......... 514/359, 360, 365, 461, 468
See application file for complete search history.

(56) References Cited

U.S. PATENT DOCUMENTS

| 5,543,415 | A  | 8/1996  | Suzuki et al. |
| 6,727,259 | B2 | 4/2004  | Shimada et al. |
| 7,880,013 | B2 | 2/2011  | Nakajima et al. |
| 7,928,098 | B2 | 4/2011  | Uesaka et al. |
| 2003/0139395 | A1 | 7/2003 | Greenlee et al. |
| 2006/0281770 | A1 | 12/2006 | Kase et al. |
| 2007/0105919 | A1 | 5/2007 | Nakajima et al. |

FOREIGN PATENT DOCUMENTS

| CN | 1976905 | 6/2007 |
| EP | 1 700 856 | 9/2006 |
| EP | 1 894 930 | 3/2008 |
| WO | 94-01114 | 1/1994 |
| WO | 99-12546 A1 | 3/1999 |
| WO | 03-022283 A1 | 3/2003 |
| WO | 2004-108137 A1 | 12/2004 |
| WO | 2005-063743 A1 | 7/2005 |
| WO | 2005/095357 | 10/2005 |
| WO | 2007-015528 A1 | 8/2007 |

OTHER PUBLICATIONS

Minor, et al., "Enhancing Brain Adenosine Signaling With the Nucleoside Transport Blocker NBTI (S-(4-Nitrobenzyl)-6-Theoinosine) Mimics the Effects of Inescapable Shock on Later Shuttle-Escape Performance in Rats", Behavioral Neuroscience, vol. 122, No. 6 (2008) 1236-47.

Sarges, et al., "4-Amino [1,2,4]troazp;p[4,3-a]quinoxalines. A Novel Class of Potent Adenosine Receptor Antagonists and Potential Rapid-Onset Antidepressants", J. Med. Chem., vol. 33, No. 8 (1990) 2240-2254.

Kanda, et al., "Adenosine A2A Antagonist: A Novel Antiparkinsonian Agent that Does Not Provoke Dyskinesia in Parkinsonian Monkeys", Annals Neurol., vol. 43, No. 4 (1998) 507-513.

Yacoubi, et al., "Adenosine A2A receptor antagonists are potential antidepressants: evidence based on pharmacology and A2A receptor knockout mice", Br. J. Pharmacol., vol. 134 (2001) 68-77.

Yacoubi, et al., "Adenosine A2A receptors and depression", Neurology, vol. 61 (Supp 6) (2003) S82-87.

Huang, et al., "Adenosine A2A, but not A1, receptors mediate the arousal effect of caffeine", Nature Neuroscience, vol. 8, No. 7 (2005) 858-859.

(Continued)

*Primary Examiner* — Yong Chong
(74) *Attorney, Agent, or Firm* — Fitzpatrick, Cella, Harper & Scinto

(57) ABSTRACT

Provided are an agent for the treatment and/or prophylaxis of a mood disorder comprising, as an active ingredient, a thiazole derivative represented by the formula (I) wherein $R^1$ represents aryl or the like, and $R^2$ represents pyridyl or the like, or a pharmaceutically acceptable salt thereof, and the like.

(I)

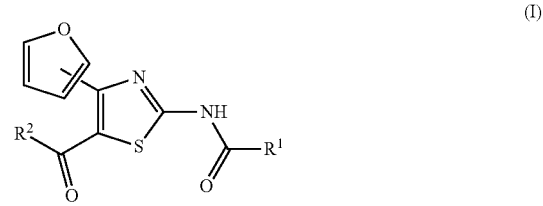

5 Claims, No Drawings

(56) References Cited

OTHER PUBLICATIONS

Jacobson, et al., "Adenosine receptors as therapeutic targets", Nature Reviews Drug Discovery, vol. 5 (2006) 247-264.

Schapira, et al., "Novel pharmacological targets for the treatment of Parkinson's disease", Nature Reviews Drug Discovery, vol. 5 (2006) 845-854.

Ferre, et al., "Adenosine A2A receptors in ventral striatum, hypothalamus and nociceptive circuitry . . . ", Progress in Neurobiology, vol. 83 (2007) 332-347.

Simola, et al., "Adenosine A2A Receptor Antagonists and Parkinson's Disease: State of the Art and Future Directions", Current Pharmaceutical Design, vol. 14 (2008) 1475-1489.

Itoh, et al., "Effects of rolipram, a phosphodiesterase 4 inhibitor, in combination with imipramine on depressive behavior, CRE-binding activity and BDNF level in learned helplessness rats", European Journal of Pharmacology, vol. 498 (2004) 135-42.

Harrison's Principles of Internal Medicine, 15th Ed., vol. 2 (2001) 2548.

Merck Manuals Professional Version, Depressive Disorders, http://www.merckmanuals.com/professional/psychiatric-disorders/mood-disorders/.

THERAPEUTIC AGENT FOR MOOD DISORDERS

This application is a National Phase of PCT application No. PCT/JP2010/064988 filed Sep. 2, 2010, which in turn is claims benefit of Japanese Application No. 202893/2009 filed Sep. 2, 2009.

TECHNICAL FIELD

The present invention relates to an agent for the treatment and/or prophylaxis of a mood disorder such as a depressive disorder (e.g., major depression, dysthymia, a depression-related syndrome), symptom of depression due to physical disorder, drug-induced symptom of depression or the like.

BACKGROUND ART

Depressive Disorders

Depressive disorders are a class of psychiatric disorders classified under mood disorders, representing a condition with some disturbance in living activity due to a persistent depressive state. Regarding the classification and diagnosis of mood disorders, information is available in the American Psychiatric Association's "Diagnostic and Statistical Manual of Mental Disorders—IV: DSM-IV-TR" and the World Health Organization's "International Statistical Classification of Diseases and Related Health Problems—10: ICD-10, F30-F39". According to the provisions of the DSM-IV-TR, mood disorders are roughly divided into bipolar disorders, which have both depressive symptoms and exaltation (manic symptoms), and depressive disorders, which involve depressive symptoms only. Bipolar disorders are classified into bipolar I disorders, which involve manic symptoms and depressive symptoms; bipolar II disorders, which involve depressive symptoms and mild manic symptoms; cyclothymic disorders, which involve mild depressive symptoms and mild manic symptoms; and bipolar disorders not otherwise specified. Depressive disorders are classified into major depressive disorders, in which a single depressive symptom is observed for 6 months or more; dysthymic disorders, in which mild depressive symptoms are observed for 2 years or more; and depression-related syndromes (minor depressive disorders, which are mildly symptomatic depressive disorders, recurrent short-term depressive disorders, in which short-term depressive symptoms are repeatedly observed, premenstrual dysphoric mood disorders, which are woman-specific physiological depressive symptoms). In addition to the aforementioned two major classes, mood disorders due to physical disorder, mood disorders due to drugs etc., mood disorders not otherwise specified and the like are classified under the category mood disorders as a whole.

Major Depressive Disorders (Major Depression)

Major depressive disorders are a disease commonly known as depression, representing a class of mood disorders. The essential feature thereof is that social activity is disturbed by long-lasting depressive symptoms. Patients with major depressive disorders can manifest common physical symptoms such as limb/back/head heaviness, back pain, headache, muscle pain, decreased physical strength, lassitude, and body weight loss. Also manifested are circulatory symptoms such as tachycardia; digestive symptoms such as dry mouth, dysgeusia, dyspepsia, diarrhea, abdominal pain, and anorexia; respiratory symptoms such as respiratory distress and hyperventilation; reproductive symptoms such as decreased libido and menstrual irregularities; urogenital symptoms such as pollakiuria and dysuria; and the like; the physical symptoms thereof encompass a broad range.

Dysthymic Disorders (Dysthymia)

Dysthymic disorders are a disease that was known as depressive hypomelancholia in the past, representing a class of mood disorders. The essential feature thereof is that social activity is disturbed by long-lasting depressive symptoms but the criteria of major depressive disorders are not met. Although dysthymic disorders involve relatively mild symptoms compared with major depressive disorders, such difference in the symptoms does not show in the degree of disturbance in social life, and both are the same in that the patients are in a pathological depressive state.

Depression-Related Syndrome

This is a syndrome proposed as defined by the DSM-IV-TR for a class that was known as mild depression in the past. Minor depressive disorders, which are mildly symptomatic depressive disorders; recurrent short-term depressive disorders, in which short-term depressive symptoms are repeatedly observed; premenstrual dysphoric mood disorders, which are woman-specific physiological depressive symptoms; and the like are included.

Mood Disorders Due to Physical Disorder (Depressive Symptoms Due to Physical Disorder)

There are some cases where depressive symptoms are manifested even when the underlying disease is not a mental disease but an internal medical disease, which are generically referred to as mood disorders due to physical disorder. Internal medical diseases include, for example, hypothyroidism, hyperparathyroidism, and Cushing's syndrome, which are endocrine diseases; systemic erythematodes and rheumatoid arthritis, which are collagen diseases; cerebral infarction and Parkinson's disease as organic cerebral diseases; infectious diseases such as by influenza or human immunodeficiency virus; and the like.

Mood Disorders Due to Drugs etc. (Drug-Induced Depressive Symptoms)

There are some cases where depressive symptoms are manifested with other drug therapies, and these are described as mood disorders due to drugs etc. Drugs known to induce depressive symptoms include, for example, reserpine, which is used as a hypotensive drug; methyl-dopa; clonidine; propranolol; hormones such as adrenocorticosteroid and progestin/estrogen mixed hormone; anti-Parkinsonian drugs such as L-dopa, amantadine hydrochloride, and bromocriptine; histamine H2 receptor antagonists such as cimetidine; interferons; cycloserine and the like.

Regarding depressive disorders, a wide variety of causes are suspected; in particular, genetic temperaments, growth and development in infancy and childhood, as well as combinations thereof with later life experiences are suspected. Depressive disorders are treated by using counseling, psychotherapy, pharmacological therapy (drug therapy) and the like singly or in combination. Drugs that are typically used to treat depressive disorder patients include, for example, tricyclic/tetracyclic antidepressants such as amitriptyline hydrochloride, imipramine hydrochloride, clomipramine hydrochloride, amoxapine, mianserin hydrochloride, maprotiline hydrochloride, and the like; selective serotonin reuptake inhibitors (SSRIs) such as paroxetine, fluvoxamine, fluoxetine, and the like; serotonin/noradrenaline uptake inhibitors (SNRIs) such as milnacipran, duloxetine, venlafaxine, and the like; and the like. Other drugs used include, for example, sulpiride, trazodone hydrochloride and the like.

On the other hand, it is known that adenosine is widely distributed in the whole body, and exhibits a variety of physiological actions on the central nervous system, the cardiac muscle, the kidneys, the smooth muscle, and the like through its receptors (see non-patent document 1).

For example, adenosine $A_1$ antagonists are known to facilitate defecation (Jpn. J. Pharmacol., Vol.68, p.119 (1995)). Further, the adenosine $A_{2A}$ receptors are known to be involved particularly in the central nervous system, and the antagonists of the adenosine $A_{2A}$ receptors are known to be useful as, for example, therapeutic drugs for Parkinson's disease etc. (see non-patent document 2), therapeutic drugs for sleep disturbance (see Nature Neuroscience, p. 858 (2005); patent document 3), therapeutic drugs for depression (see non-patent document 3) and the like. There are many reports concerning the relationship between adenosine receptors and Parkinson's disease (Nature Reviews Drug Discovery, 5, p.845 (2006); Current Pharmaceutical Design, 14, p.1475 (2008)).

Regarding the association between adenosine $A_{2A}$ receptors and depressive symptoms, an investigation using mice deficient in adenosine $A_{2A}$ receptors led to a report that adenosine $A_{2A}$ receptor antagonistic activity induces behavioral pharmacological changes similar to those with administration of antidepressants (see Non-patent Document 4). Xanthine compounds having adenosine $A_{2A}$ receptor antagonistic activity are known to possess antidepressive activity (for example, WO94/01114), and are known to further possess anti-Parkinsonian activity (for example, Ann. Neurol., 43, p. 507 (1998)), therapeutic effects on anxiety disorders (for example, WO2004/108137), suppressing activity against neurodegeneration (for example, WO99/12546) and the like. Combinations of adenosine $A_{2A}$ receptor antagonists and antidepressants or anxiolytics have been reported (see Patent Document 1).

On the other hand, for example, compounds represented by the formulas (IA), (IB), (IC), (ID) and the like are known to have affinity to adenosine $A_{2A}$ receptors and have a therapeutic effect for Parkinson's disease (see patent document 2). It is also known that these compounds are useful as an agent for the treatment and/or prophylaxis of sleep disturbance (see patent document 3).

(IA)

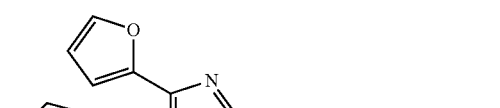
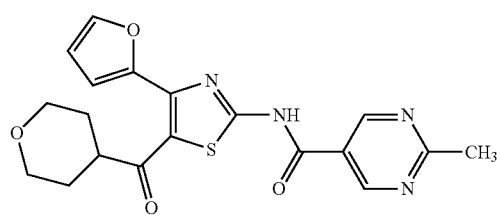
(IB)

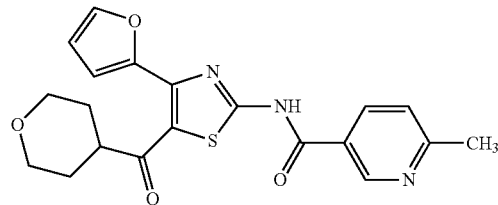
(IC)

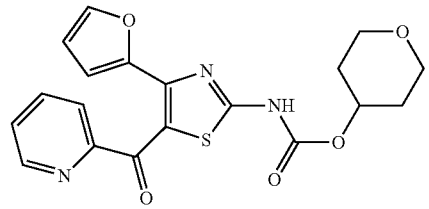
(ID)

DOCUMENT LIST

Patent Documents patent document 1: WO2003/022283
patent document 2: WO2005/063743
patent document 3: WO2007/015528

Non-Patent Documents non-patent document 1: Nature Reviews Drug Discovery, 2006, vol. 5, p. 247 non-patent document 2: Progress in Neurobiology, 2007, vol. 83, p. 332 non-patent document 3: Neurology, 2003, vol. 61 (11 Suppl 6), S82-7 non-patent document 4: Br. J. Pharmacol., 2001, vol. 134, p.68

SUMMARY OF THE INVENTION

Problems to be Solved by the Invention

An object of the present invention is to provide an agent for the treatment and/or prophylaxis of a mood disorder such as a depressive disorder (e.g., major depression, dysthymia, a depression-related syndrome or the like), symptom of depression due to physical disorder, drug-induced symptom of depression or the like.

Means of Solving the Problems

The present invention relates to the following (1)-(22).
(1) An agent for the treatment and/or prophylaxis of a mood disorder, comprising a thiazole derivative represented by the formula (I)

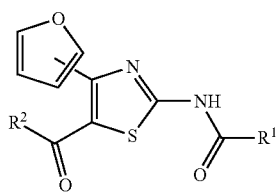

(I)

wherein R¹ represents aryl, aralkyl, an aromatic heterocyclic group, aromatic heterocyclyl-alkyl, aliphatic heterocyclyl-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof as an active ingredient.

(2) The agent for the treatment and/or prophylaxis of a mood disorder, comprising the thiazole derivative or the pharmaceutically acceptable salt thereof of (1), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.

(3) The agent for the treatment and/or prophylaxis of a mood disorder, comprising the thiazole derivative or the pharmaceutically acceptable salt thereof of (1), wherein R¹ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(4) The agent for the treatment and/or prophylaxis of a mood disorder, comprising the thiazole derivative or the pharmaceutically acceptable salt thereof of any one of (1)-(3), wherein R² is pyridyl.

(5) The agent for the treatment and/or prophylaxis of a mood disorder, comprising the thiazole derivative or the pharmaceutically acceptable salt thereof of any one of (1)-(3), wherein R² is tetrahydropyranyl.

(6) The agent for the treatment and/or prophylaxis of a mood disorder, comprising the thiazole derivative or the pharmaceutically acceptable salt thereof of (1), wherein the thiazole derivative represented by the formula (I) is a compound represented by any one of the following formulas (IA)-(IAA).

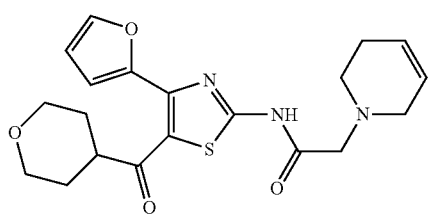

(IA)

-continued

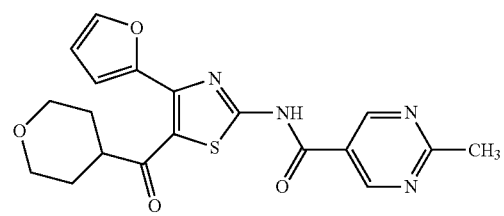

(IB)

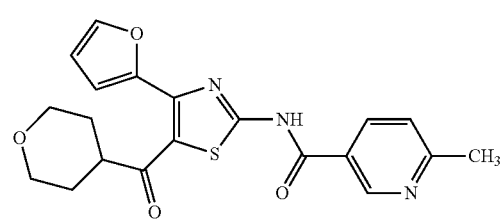

(IC)

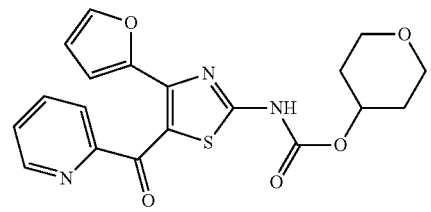

(ID)

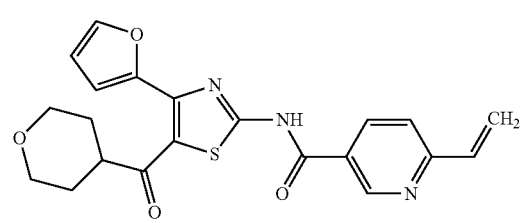

(IE)

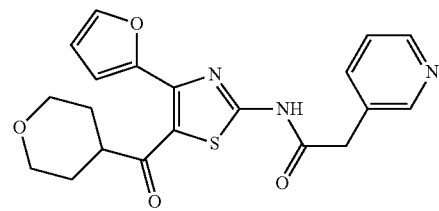

(IF)

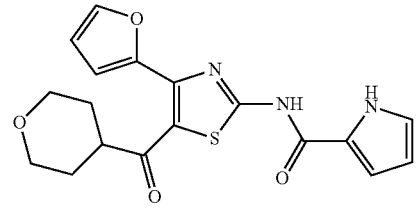

(IG)

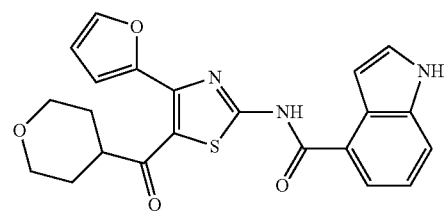

(IH)

(II)
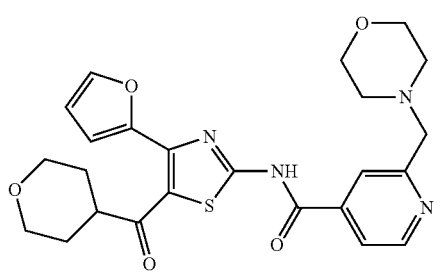
(IJ)
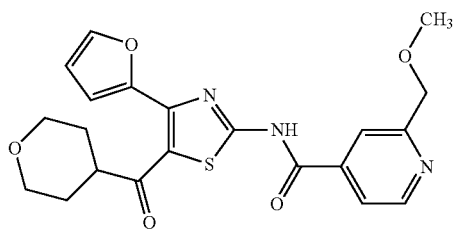
(IK)
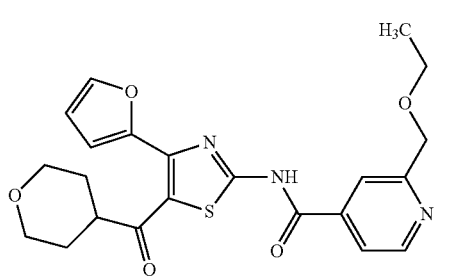
(IL)
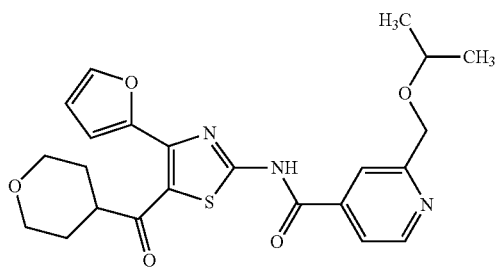
(IM)
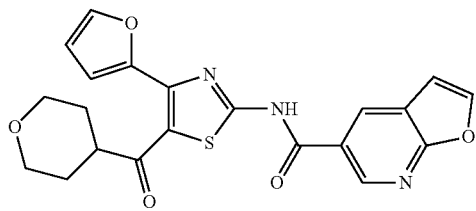
(IN)
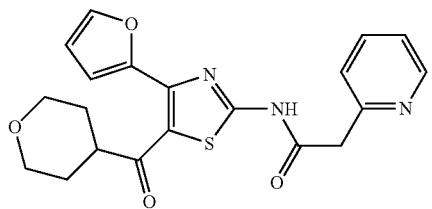
(IO)
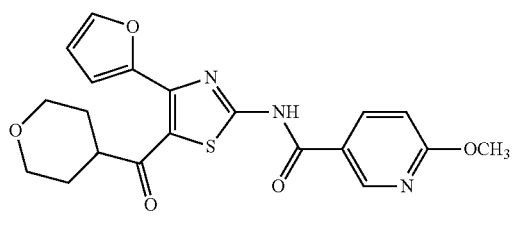
(IP)
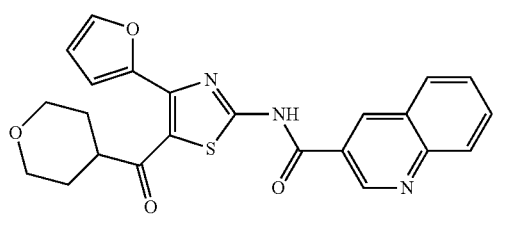
(IQ)
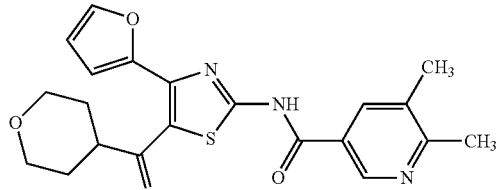
(IR)
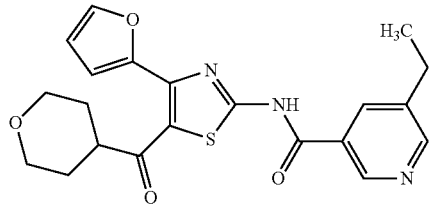
(IS)
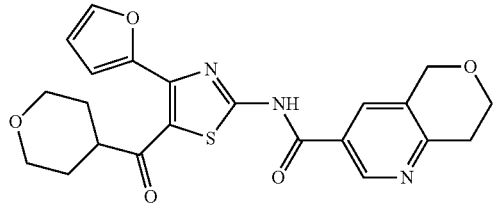
(IT)
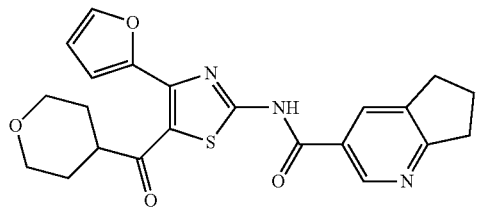
(IU)
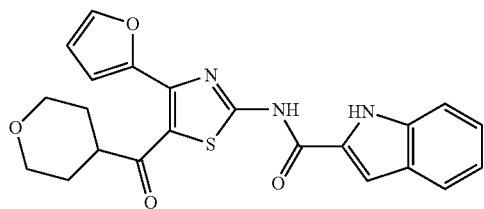

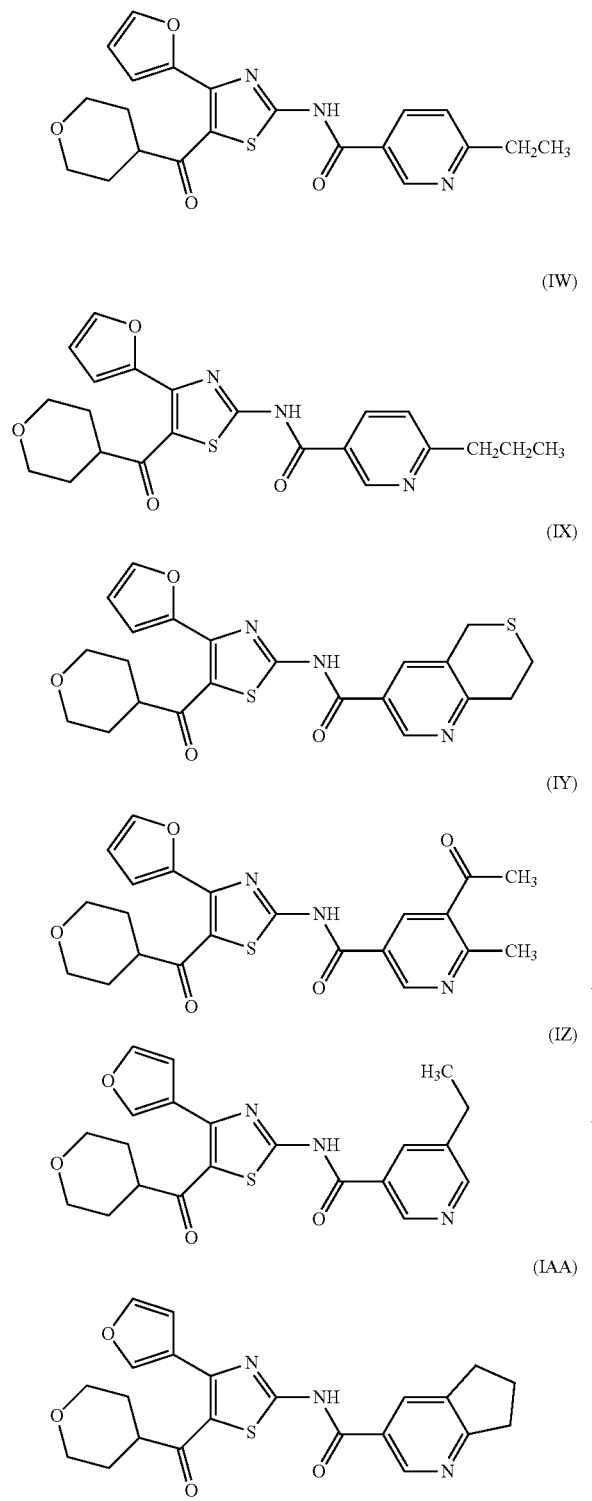

(7) The agent for the treatment and/or prophylaxis of a mood disorder, comprising the thiazole derivative or the pharmaceutically acceptable salt thereof of (1), wherein the thiazole derivative represented by the formula (I) is a compound represented by any one of the following formulas (IA)-(ID).

(8) The agent of any of (1)-(7), wherein the mood disorder is a depressive disorder.

(9) The agent of any of (1)-(7), wherein the mood disorder is major depression, dysthymia, a depression-related syndrome, a symptom of depression due to a physical disorder or a drug-induced symptom of depression.

(10) The agent of any of (1)-(7), wherein the mood disorder is major depression.

(11) A method of treating and/or preventing a mood disorder, comprising administering an effective amount of the thiazole derivative of any of the above-mentioned (1)-(7) or the pharmaceutically acceptable salt thereof.

(12) The method of (11), wherein the mood disorder is a depressive disorder.

(13) The method of (11), wherein the mood disorder is major depression, dysthymia, a depression-related syndrome, a symptom of depression due to a physical disorder or a drug-induced symptom of depression.

(14) The method of (11), wherein the mood disorder is major depression.

(15) The thiazole derivative of any of the above-mentioned (1)-(7) or the pharmaceutically acceptable salt thereof, for use in the treatment and/or prophylaxis of a mood disorder.

(16) The thiazole derivative of (15) or a pharmaceutically acceptable salt thereof, wherein the mood disorder is a depressive disorder.

(17) The thiazole derivative of (15) or the pharmaceutically acceptable salt thereof, wherein the mood disorder is major depression, dysthymia, a depression-related syndrome, a symptom of depression due to a physical disorder or a drug-induced symptom of depression.
(18) The thiazole derivative of (15) or the pharmaceutically acceptable salt thereof, wherein the mood disorder is major depression.
(19) Use of the thiazole derivative of any of the above-mentioned (1)-(7) or the pharmaceutically acceptable salt thereof, for the manufacture of an agent for the treatment and/or prophylaxis of a mood disorder.
(20) The use of (19), wherein the mood disorder is a depressive disorder.
(21) The use of (19), wherein the mood disorder is major depression, dysthymia, a depression-related syndrome, a symptom of depression due to a physical disorder or a drug-induced symptom of depression.
(22) The use of (19), wherein the mood disorder is major depression.

Effect of the Invention

The present invention provides an agent for the treatment and/or prophylaxis of a mood disorder such as a depressive disorder (e.g., major depression, dysthymia, a depression-related syndrome or the like), symptom of depression due to physical disorder, drug-induced symptom of depression or the like, which comprises a thiazole derivative or a pharmaceutically acceptable salt thereof as an active ingredient, and the like.

MODE FOR CARRYING OUT THE INVENTION

In the following, the compound represented by the formula (I) is sometimes referred to as compound (I). The compounds having other formula numbers are also referred to in the same manner.

The definition of each group in the formula (I) is as follows.

Examples of the lower alkyl moiety of the lower alkyl, the lower alkoxy and the lower alkanoyl include straight or branched alkyl having 1 to 10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the aralkyl include aralkyl having 7 to 16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of the aryl include aryl having 6 to 14 carbon atoms, and more specific examples thereof include phenyl, naphthyl, azulenyl, anthryl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic fused aromatic heterocyclic group in which 3 to 8-membered rings are fused, having at least one atom selected from a nitrogen atom, an oxygen atom and a sulfur atom, and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, furo[2,3-b]pyridyl, 6,7-dihydro-5H-cyclopenta[b]pyridyl, 7,8-dihydro-5H-pyrano[4,3-b]pyridyl, 7,8-dihydro-5H-thiopyrano[4,3-b]pyridyl and the like.

Examples of the aromatic heterocyclyl-alkyl include a group wherein an aromatic heterocyclic group is bonded to alkylene. The aromatic heterocyclic group include those exemplified in the above-mentioned aromatic heterocyclic group, and examples of the alkylene include alkylene having 1 to 10 carbon atoms, and specific examples thereof include methylene, ethylene, trimethylene, propylene, tetramethylene, pentamethylene, hexamethylene, heptamethylene, octamethylene, nonamethylene, decamethylene and the like. Specific examples of the aromatic heterocyclyl-alkyl include pyrrolylmethyl, pyrrolylethyl, thiazolylmethyl, pyridylmethyl, pyridylethyl, pyrimidinylmethyl, pyrimidinylethyl, indolylmethyl, benzimidazolylmethyl and the like.

Examples of the aliphatic heterocyclyl-alkyl include a group wherein the aliphatic heterocyclic group is bonded to alkylene. Examples of the aliphatic heterocyclic group include a 5-membered or 6-membered monocyclic aliphatic heterocyclic group containing at least one atom selected from a nitrogen atom, an oxygen atom and a sulfur atom, a bicyclic or tricyclic fused aliphatic heterocyclic group in which 3 to 8-membered rings are fused, having at least one atom selected from a nitrogen atom, an oxygen atom, and a sulfur atom, and the like. More specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, 5,6-dihydro-2H-pyridyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like. Examples of the alkylene include alkylene having 1 to 10 carbon atoms, and specific examples thereof include methylene, ethylene, trimethylene, propylene, tetramethylene, pentamethylene, hexamethylene, heptamethylene, octamethylene, nonamethylene, decamethylene and the like. Specific examples of the aliphatic heterocyclyl-alkyl include 5,6-dihydro-2H-pyridylmethyl, 5,6-dihydro-2H-pyridylethyl, tetrahydro-2H-pyranylmethyl, 5,6-dihydro-2H-pyranylmethyl, 5,6-dihydro-2H-pyranylethyl, morpholinomethyl, morpholinoethyl, piperazinylmethyl, oxazolidinylmethyl and the like.

The halogen means each atom of fluorine, chlorine, bromine and iodine.

Compound (I) or a pharmaceutically acceptable salt thereof used in the present invention is preferably a compound having a potent antagonistic activity against adenosine $A_{2A}$ receptors from among various subtypes of adenosine receptors (e.g., adenosine $A_1$, $A_{2A}$, $A_{2B}$ and $A_3$ receptors).

Accordingly, compound (I) or a pharmaceutically acceptable salt thereof in the present invention is preferably a compound having a strong affinity for the adenosine $A_{2A}$ receptors. For example, the compound is preferably one having an inhibitory activity of 50% or more at a test compound concentration of $3 \times 10^{-8}$ mol/L, more preferably one having an inhibitory activity of 50% or more at a test compound concentration of $1 \times 10^{31\ 8}$ mol/L, still more preferably one having an inhibitory activity of 50% or more at a test compound concentration of $3\times10^{-9}$ mol/L, further preferably one having an inhibitory activity of 50% or more at a test compound concentration of $1\times10^{-9}$ mol/L, in the adenosine $A_{2A}$ receptor binding test shown in the below-mentioned Test Example 1. In addition, the compound is preferably one having an inhibitory activity of 30 nmol/L or less in an inhibitory constant (Ki value) obtained by the test, more preferably one having an inhibitory activity of 10 nmol/L or less, still more preferably one having an inhibitory activity of 3 nmol/L or less, further preferably one having an inhibitory activity of 1 nmol/L or less.

Further, compound (I) or a pharmaceutically acceptable salt thereof used in the present invention is preferably a compound having selective affinity for the adenosine $A_{2A}$ receptors from among various subtypes of the adenosine receptors. For example, a compound having a higher affinity for the adenosine $A_{2A}$ receptors than that for the adenosine $A_1$ receptors is preferable. Specifically, for example, the compound is preferably a compound having 5 times or more affinity, more preferably 10 times or more affinity, further preferably 50 times or more affinity, even more preferably 100 times or more affinity, most preferably 500 times or more affinity for the adenosine $A_{2A}$ receptors as compared to that for the adenosine $A_1$ receptors (e.g., compared at Ki value).

The affinity can be determined according to a conventional method, for example, according to the method of Test Example 1 to be mentioned below, or the methods described in a document [for example, Naunyn Schmiedebergs Arch Pharmacol., 355(1), p. 59 (1987); Naunyn Schmiedebergs Arch Pharmacol. 355(2), p. 204 (1987); Br. J. Pharmacol. 117(8), p. 1645 (1996) and the like].

More specifically, compound (I) is preferably a compound wherein $R^1$ is phenyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; pyridyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; pyrimidinyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; 5,6-dihydro-2H-pyridylmethyl optionally substituted by 1 to 3 substituents selected from halogen, $C_{1-6}$ alkyl and $C_{1-6}$ alkoxy; 2,3,4,5-tetrahydropyranyloxy; pyrrolyl; indolyl; oxazolopyridyl; quinolyl; 1H-3,4-dihydropyranopyridinyl; 1H-3,4-dihydrothiopyranopyridinyl; cyclopentapyridyl; or pyridylmethyl,
more preferably a compound wherein Fe is phenyl optionally substituted by 1 to 3 substituents selected from a fluorine atom, a chlorine atom, methyl and methoxy; pyridyl optionally substituted by 1 to 3 substituents selected from a fluorine atom, a chlorine atom, methyl and methoxy; pyrimidinyl optionally substituted by 1 to 3 substituents selected from a fluorine atom, a chlorine atom, methyl and methoxy; 5,6-dihydro-2H-pyridylmethyl optionally substituted by 1 to 3 substituents selected from a fluorine atom, a chlorine atom, methyl and methoxy; or 2,3,4,5-tetrahydropyranyloxy, still more preferably a compound wherein $R^1$ is pyridyl substituted by 1 to 3 substituents selected from a chlorine atom, methyl and methoxy; pyrimidinyl substituted by 1 to 3 substituents selected from chlorine atom, methyl and methoxy; 5,6-dihydro-2H-pyridylmethyl; or 2,3,4,5-tetrahydropyranyloxy. More specifically, compound (I) is preferably, for example, compounds of the following formulas (IA)-(IAA), and the like.

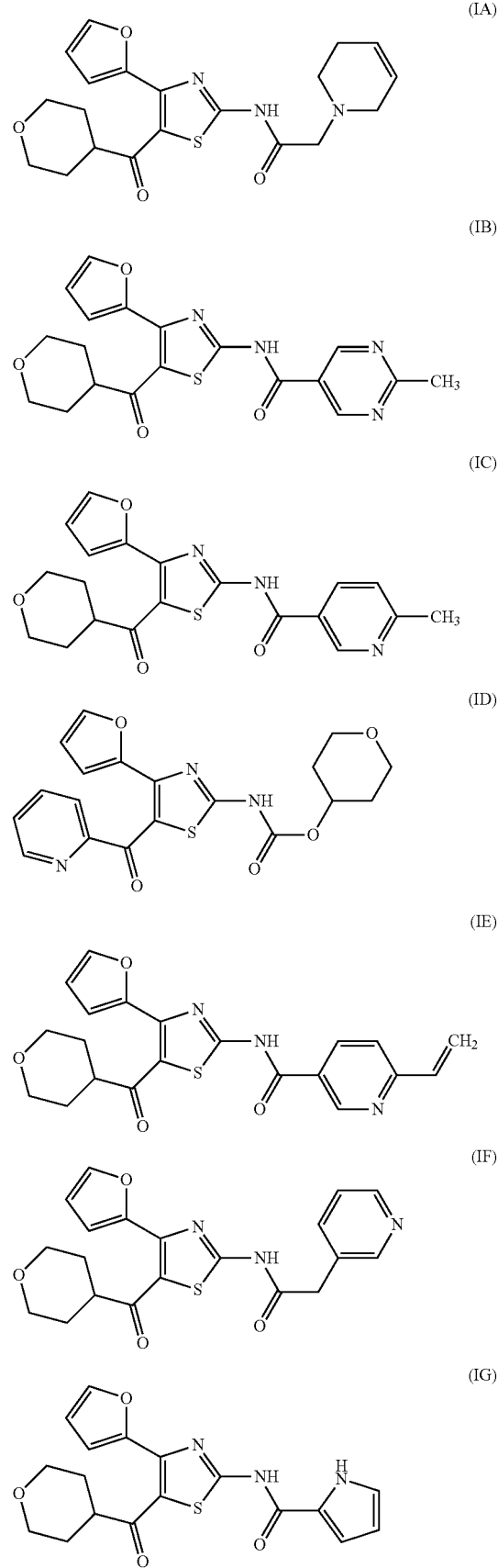

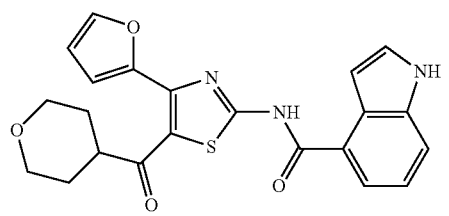
(IH)
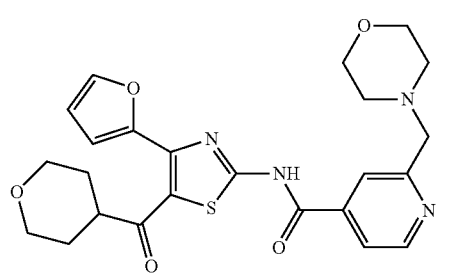
(II)
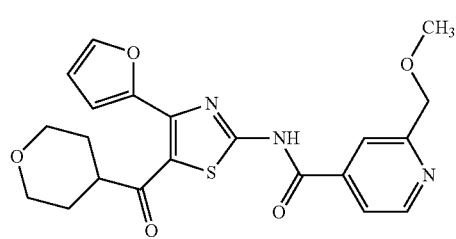
(IJ)
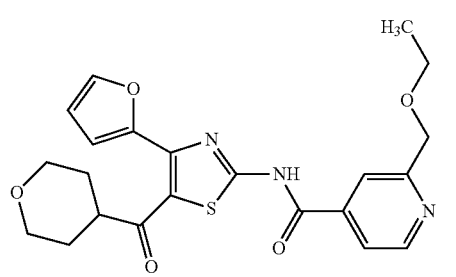
(IK)
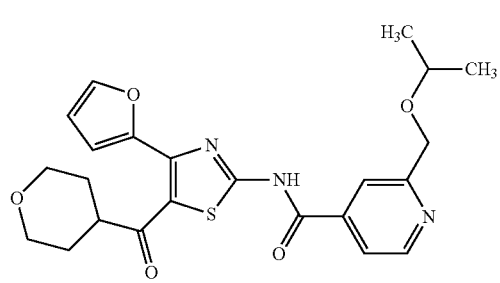
(IL)
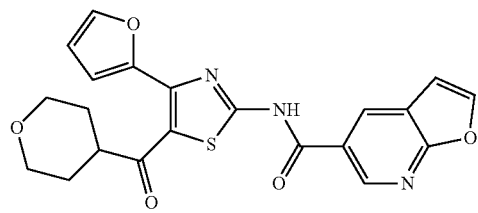
(IM)
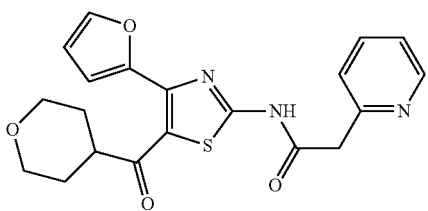
(IN)
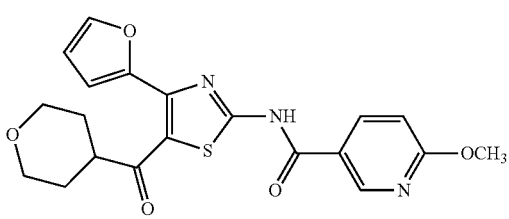
(IO)
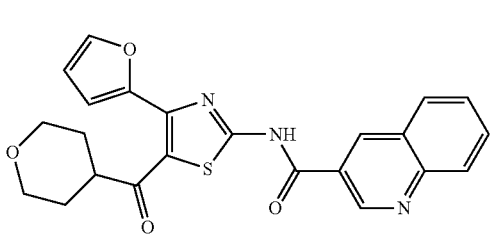
(IP)
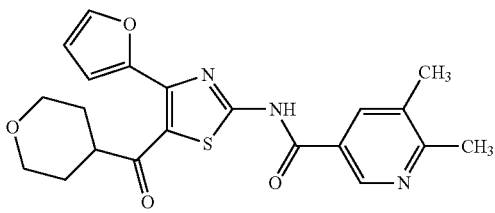
(IQ)
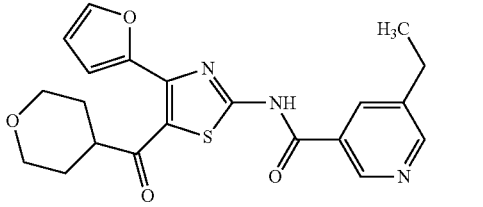
(IR)
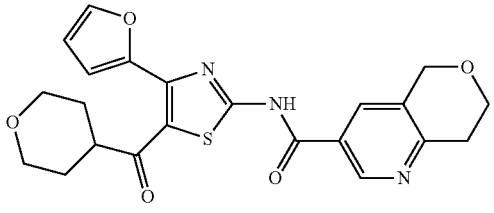
(IS)
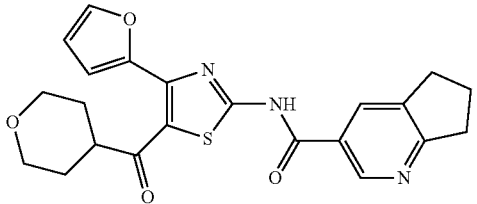
(IT)

-continued

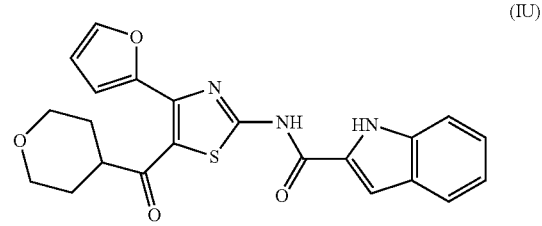
(IU)

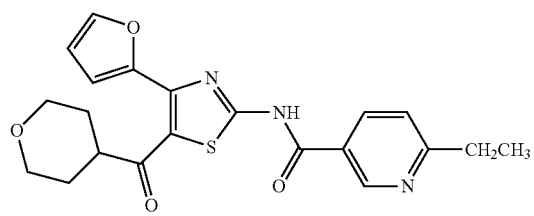
(IV)

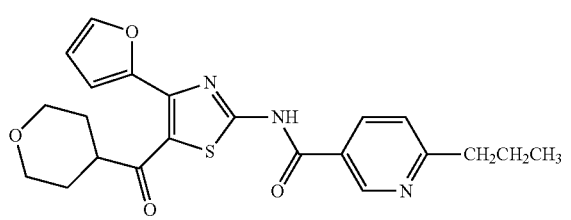
(IW)

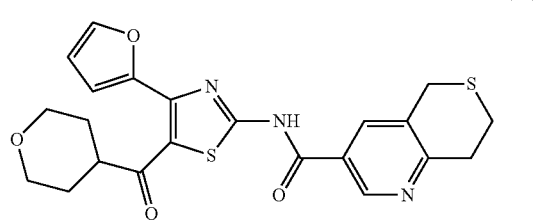
(IX)

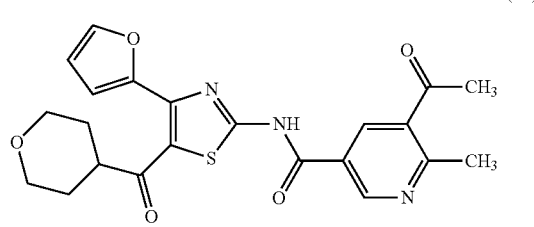
(IY)

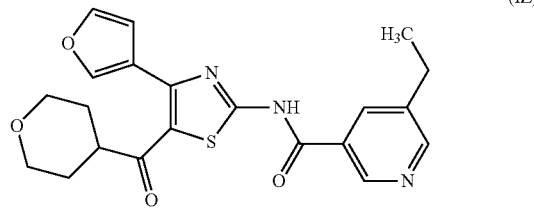
(IZ)

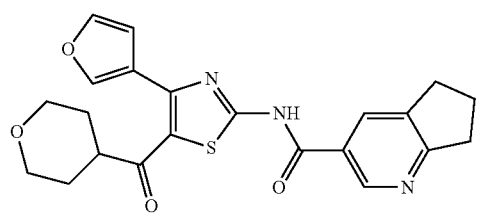
(IAA)

The pharmaceutically acceptable salts of compound (I) include, for example, pharmaceutically acceptable acid addition salts, metal salts, ammonium salts, organic amine addition salts, amino acid addition salts, and the like. The pharmaceutically acceptable acid addition salts of compound (I) include, for example, inorganic acid salts such as hydrochloride, hydrobromate, nitrate, sulfate, and phosphate; organic acid salts such as acetate, oxalate, maleate, fumarate, citrate, benzoate, and methane sulfonate, and the like. Examples of the pharmaceutically acceptable metal salts include alkali metal salts such as a sodium salt, and a potassium salt; alkaline earth metal salts such as a magnesium salt, and a calcium salt; an aluminum salt; a zinc salt, and the like. Examples of the pharmaceutically acceptable ammonium salts include salts of ammonium, tetramethylammonium, and the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

Compound (I) can be produced according to a known method, for example, the method described in WO 2005/063743 and the like.

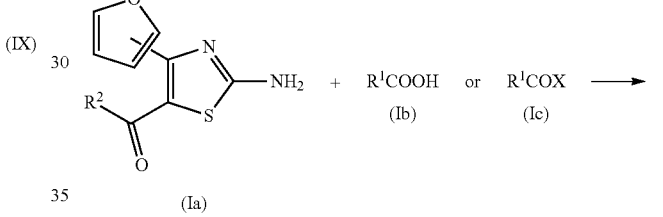
(Ia)

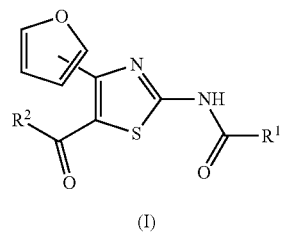
(I)

wherein $R^1$ and $R^2$ are as defined above, and X represents a chlorine atom, a bromine atom or the like.

Specifically, as shown in the above-mentioned formula, compound (I) can be produced, for example, by reacting compound (Ia) described in WO 2005/063743 with preferably 0.5 to 5 equivalents of compound (Ib) in a solvent such as methanol, dichloromethane, chloroform, toluene, ethyl acetate, acetonitrile, tetrahydrofuran (THF), N,N-dimethylformamide (DMF), N,N-dimethylacetamide (DMA), pyridine, water, or a mixed solvent thereof and the like, preferably in the presence of 1 to 5 equivalents of a condensing agent such as 1,3-dicyclohexanecarbodiimide (DCC), 1-ethyl-3-(3-dimethylaminopropyl)carbodiimide (EDC) hydrochloride and the like, if necessary, in the presence of preferably 1 to 5 equivalents of 1-hydroxybenzotriazole (HOBt) monohydrate, 4-dimethylaminopyridine (DMAP) and the like, at a temperature between −20° C. and the boiling point of the solvent used, for 5 min to 72 hr.

Alternatively, compound (I) can also be produced, for example, by reacting compound (Ia) described in WO 2005/

063743 with preferably 1 to 10 equivalents of compound (Ic) without solvent or in a solvent such as dichloromethane, chloroform, 1,2-dichloroethane, toluene, ethyl acetate, acetonitrile, THF, DMF, DMA, pyridine and the like, if necessary, in the presence of preferably 1 to 10 equivalents of a base such as potassium carbonate, triethylamine, 4-dimethylaminopyridine (DMAP) and the like, at a temperature between −20° C. and 150° C., for 5 min to 72 hr.

Compound (I) may exist as stereoisomers such as geometrical isomers or optical isomers, or tautomers. Any possible isomers and a mixture thereof, including those mentioned above, can be used for the agent of the present invention for the treatment and/or prophylaxis of a mood disorder.

To obtain a salt of compound (I), when the compound (I) is obtained in the form of a salt, it may be purified as it is. Further, when the compound is obtained in a free form, compound (I) may be dissolved or suspended in a suitable solvent, followed by addition of an acid or a base to form a salt. Then, the resulting salt may be isolated and purified.

The compound (I) or a pharmaceutically acceptable salt thereof may exist in the form of an adduct with water or various solvents. Such adduct can also be used for the agent of the present invention for the treatment and/or prophylaxis of a mood disorder.

A pharmacological action of the representative compound (I) is now specifically explained by way of Experimental Examples.

TEST EXAMPLE 1

Adenosine Receptor Binding Action (1) Adenosine $A_{2A}$ Receptor Binding Test

The test can be performed according to, for example, the method of Varani et al. (British Journal of Pharmacology, 117, p. 1693 (1996)).

Specifically, for example, human recombinant Adenosine $A_{2A}$ receptors are expressed in HEK-293 cells. The cell membranes of the receptor-expressing cells are collected, and a cell membrane suspension is prepared. After dilution with tris(hydroxymethyl)-aminomethane hydrochloride (Tris HCl) buffer, tritium-labeled 2-[p-(2-carboxyethyl)phenethylamino]-5'-(N-ethylcarboxamido)adenosine ($^3$H-CGS21680: 50 mmol/L) and a test compound solution (dimethyl sulfoxide solution of the test compound) are added to the cell membrane suspension for binding to the receptors. After the reaction, the mixture is subjected to rapid suction filtration using glass-fiber filter paper, and the radioactivity of the glass-fiber filter paper is measured. In this way, the inhibitory rate of the test compound for the human adenosine $A_{2A}$ receptor binding ($^3$H-CGS21680 binding) can be determined.

The test can also be performed according to the method of Bruns et al. (Molecular Pharmacology, Vol. 29, p. 331, 1986).

Specifically, for example, rat striatum is suspended in 50 mL of ice-cooled Tris HCl buffer (50 mmol/L, pH 7.7) using a Polytron homogenizer and the suspension is centrifuged. The resulting precipitate is resuspended by adding Tris HCl buffer (50 mmol/L) thereto, followed by centrifugation in the same manner. The resulting final precipitate is suspended in Tris HCl buffer (50 mmol/L) [containing magnesium chloride (10 mmol/L), and adenosine deaminase (0.02 units/mg tissue)] to prepare the suspension at the tissue concentration of 5 mg (wet weight)/mL. Tritium-labeled CGS-21680 (final concentration of 6.0 mmol/L), and the test compound solution (dimethyl sulfoxide solution of test compound diluted with Tris HCl buffer) are added. The mixture is allowed to stand at 25° C. for 120 minutes, followed by rapid suction filtration using glass-fiber filter paper, and then immediately washed with ice-cooled Tris HCl buffer (50 mmol/L). The glass-fiber filter paper is then placed in a vial, and MicroScinti (PKI) is added. Then, the radioactivity is measured with a TopCount (PerkinElmer), whereby the inhibitory rate for rat adenosine $A_{2A}$ receptor binding ($^3$H-CGS21680 binding) of the test compound can be determined.

The inhibitory rate can be calculated by the following equation.

$$\text{Inhibitory rate}(\%) = \left(1 - \frac{\text{Amount of binding in the presence of drug} - \text{Amount of non-specific binding}}{\text{Total amount of binding} - \text{Amount of non-specific binding}}\right) \times 100 \quad \text{[Equation 1]}$$

In the equation, the total amount of binding refers to the bound radioactivity of $^3$H-CGS21680 in the absence of the test compound. The amount of non-specific binding refers to the bound radioactivity of $^3$H-CGS21680 in the presence of 50 μmol/L of 5'-N-ethylcarboxamideadenosine (NECA) or 100 μmol/L of cyclopentyladenosine (CPA). The amount of binding in the presence of drug refers to the bound radioactivity of $^3$H-CGS21680 in the presence of the test compound.

In the above test, the inhibitory rate for the adenosine $A_{2A}$ receptors at different concentrations of the test compound or a pharmaceutically acceptable salt thereof, and the test compound concentration at which the test compound inhibits binding by 50% ($IC_{50}$) can be calculated by appropriately adjusting the concentration of the test compound.

The inhibition constant (Ki value) of the test compound for the adenosine $A_{2A}$ receptor binding can be calculated according to the following equation.

$$Ki = IC_{50}/(1 + L/Kd) \quad \text{[Equation 2]}$$

In the equation, L denotes the concentration of the $^3$H-CGS21680 used in the test, and Kd is the dissociation constant of the $^3$H-CGS21680 used in the test.

Instead of $^3$H-CGS21680, $^3$H-5-amino-7-(2-phenylethyl)-2-(2-furyl)pyrazolo[4,3-e]-1,2,4-triazolo[1,5-c]pyrimidine ($^3$H-SCH58261) and the like may be used.

(2) Adenosine $A_1$ Receptor Binding Test

The inhibition constant (Ki value) of the test compound for the adenosine $A_1$ receptors can be calculated in the same manner as in (1), using the materials below.

Specifically, for example, human $A_1$ receptor-expressing CHO cell membranes are used, and, as the labeled compound, for example, tritium-labeled 1,3-dipropyl-8-cyclopentylxanthine ($^3$H-DPCPX) is used. The amount of non-specific binding can be determined by measuring the $^3$H-DPCPX bound radioactivity in the presence of, for example, 100 μmol/L of (-)-$N^6$-2-phenylisopropyl adenosine (R(-)-PIA). The affinity of the test compound for the human adenosine $A_1$ receptors can be confirmed in this manner.

Alternatively, for example, rat $A_1$ receptor-expressing cell membrane (PerkinElmer) is used, and as the labeled compound, for example, tritium-labeled $N^6$-cyclohexyladenosine ($^3$H-CHA) is used. For the measurement of the amount of non-specific binding, $^3$H-CHA bound radioactivity is measured in the presence of, for example, 10 μmol/L of DPCPX, and the affinity of the test compound for the rat adenosine $A_1$ receptors can be confirmed.

By the foregoing tests (1) and (2), the selective affinities of the thiazole derivative or a pharmaceutically acceptable salt thereof used in the present invention for the adenosine $A_{2A}$ receptors can be confirmed.

(3) Affinity of Compound (I) or a Pharmaceutically Acceptable Salt Thereof for Adenosine Receptors Some of the examples of the affinities of compound (I) or a pharmaceutically acceptable salt thereof for the adenosine $A_1$ receptors and the adenosine $A_{2A}$ receptors are presented below. Note that the test results below are those measured by MDS Pharma Services Inc. according to the foregoing methods.

TABLE 1

The affinity for adenosine receptor

| Compound No. | inhibitory rate* for human adenosine $A_{2A}$ receptor binding ($^3$H-CGS21680 binding) | inhibitory rate* for human adenosine $A_1$ receptor binding ($^3$H-DPCPX binding) |
| --- | --- | --- |
| (IA) | 92% | 14% |
| (IB) | 98% | 4% |
| (IC) | 88% | 29% |
| (ID) | 100% | 28% |

*inhibitory rate for compound 100 nmol/L

The above-mentioned test has confirmed that compound (I) shows selective affinity for the adenosine $A_{2A}$ receptors.

TEST EXAMPLE 2

Adenosine Receptor Binding Activity (2)

In the same manner as in the above-mentioned Test Example 1, the affinity of compound (IE)-(IAA) for adenosine receptors was confirmed (test results were those measured by Ricerca Biosciences, LLC according to the foregoing methods).

From the above tests, it has been confirmed that compound (I) shows selective affinity for the adenosine $A_{2A}$ receptors.

TEST EXAMPLE 3

Effect of Compound (I) or a Pharmaceutically Acceptable Salt Thereof on the Forced Swim Method The forced swim test in rats and mice is widely used for test system which evaluates antidepressant activities (Arch. Int. Pharmacodyn. Ther. 229, p.327 (1977)). The forced swim test is means for evaluating depressive state using the length of time during which the animal ceases its escape behavior due to a sense of helplessness (immobility time) as an index thereof by placing a mouse or a rat in water in an inescapable cylinder. Since immobility time is shortened by existing antidepressants, this is known as an animal model of depression.

Evaluation Using Mice

The male ddY-strain mice (20 to 29 g; Japan SLC, Inc.) were used in this study. A transparent acrylic water bath 10 cm in diameter and 25 cm in height was filled with water at 23° C.±1° C. to a depth of 10 cm. Each mouse was slowly placed in the water bath. At 2 minutes after placement in the bath, immobility time (duration during which no escape behavior was observed) was measured for 4 minutes.

Evaluation Using Rats

The male SD-strain rats (200 to 270 g; Charles River Japan Inc.) were used in this study. A transparent acrylic water bath 18 cm in diameter and 40 cm in height was filled with water at 25° C.±1° C. to a depth of 19 cm. Each rat was slowly placed in the water bath, allowed to stand for 15 minutes, then removed from the bath and dried with a piece of paper towel. The animals were then dried under a table light for 15 minutes and returned to the respective cages (induction of pathological condition). On the following day, the rats were slowly placed in the same water bath. Immediately, immobility time was measured for 5 minutes.

Results

Evaluation Using Mice

The test compound was used for the test in suspension in distilled water for injection (manufactured by Otsuka Phar-

TABLE 2

The affinity for adenosine receptor

| Compound No. | inhibitory rate* for human adenosine $A_{2A}$ receptor binding ($^3$H-CGS21680 binding) | inhibitory rate* for human adenosine $A_1$ receptor binding ($^3$H-DPCPX binding) | Compound No. | inhibitory rate* for human adenosine $A_{2A}$ receptor binding ($^3$H-CGS21680 binding) | inhibitory rate* for human adenosine $A_1$ receptor binding ($^3$H-DPCPX binding) |
| --- | --- | --- | --- | --- | --- |
| (IE) | 93% | 33% | (IF) | 107% | 50% |
| (IG) | 102% | 91% | (IH) | 98% | 67% |
| (II) | 85% | 19% | (IJ) | 93% | 21% |
| (IK) | 92% | 24% | (IL) | 85% | 20% |
| (IM) | 98% | 47% | (IN) | 93% | 21% |
| (IO) | 97% | 56% | (IP) | 98% | 18% |
| (IQ) | 100% | 18% | (IR) | 107% | 30% |
| (IS) | 90% | 10% | (IT) | 91% | 37% |
| (IU) | 110% | 36% | (IV) | 98% | 23% |
| (IW) | 98% | 23% | (IX) | 101% | 18% |
| (IY) | 97% | 8% | (IZ) | 102% | 21% |
| (IAA) | 98% | 9% | | | |

*inhibitory rate for compound 100 nmol/L maceutical Co.,) containing 0.5 w/v % MC (methylcellulose). The suspension containing the test compound was orally administered 1 hour before the test (0.1 mL per 10 g of mouse body weight) (test compound dose group). For a vehicle control group, a solution not containing the test compound [distilled water for injection (manufactured by Otsuka Pharmaceutical Co.,) containing 0.5 w/v % MC] was orally administered 1 hour before the test (0.1 mL per 10 g of mouse body weight).

The antidepressant activity of the test compound was evaluated with the immobility time for the vehicle control group and that for the test compound dose group as indexes. A calculation of significant difference between the dosing groups was made by Steel test after Kruskal-Wallis test was performed between the vehicle control group and the test compound dose group using statistical analysis software SAS. Table 3 shows the immobility times for the compound (IC) 0.1 mg/kg dose group and the vehicle control group.

TABLE 3

Effect of compound (IC) on immobility time in the forced swim test in mice

| treatment | immobility time (sec) | number of animals |
| --- | --- | --- |
| vehicle | 179.0 ± 15.2 | 10 |
| compound (IC) 0.1 mg/kg | 53.1 ± 11.0 | 10 |

Evaluation Using Rats

The test compound was used for the test in suspension in distilled water for injection (manufactured by Otsuka Pharmaceutical Co.,) containing 0.5 w/v % MC (methylcellulose). The suspension containing the test compound was orally administered 1 hour before the test (0.5 mL per 100 g of rat body weight) (test compound dose group). For a vehicle control group, a solution not containing the test compound [distilled water for injection (manufactured by Otsuka Pharmaceutical Co.,) containing 0.5 w/v % MC] was orally administered 1 hour before the test (0.5 mL per 100 g of rat body weight).

The antidepressive action of the test compound was evaluated with the immobility time for the vehicle control group and that for the test compound dose group as indexes. A calculation of significant difference between the dosing groups was made by Steel test after Kruskal-Wallis test was performed between the vehicle control group and the test compound dose group using statistical analysis software SAS. Table 4 shows the immobility times for the compound (IC) 0.1 mg/kg dose group and the vehicle control group.

TABLE 4

Effect of compound (IC) on immobility time in the forced swim test in rats

| treatment | immobility time (sec) | number of animals |
| --- | --- | --- |
| vehicle | 204.0 ± 21.0 | 10 |
| compound (IC) 0.1 mg/kg | 81.5 ± 15.1 | 10 |

In the compound (IC) dose group, the immobility time shortened compared with that for the vehicle control group in both the mouse and rat. From the above, it was considered that the compound (I) having a selective affinity for adenosine $A_{2A}$ receptors, or a pharmaceutically acceptable salt thereof is useful in the treatment and/or prevention of depressive disorders.

TEST EXAMPLE 4

Effect of Compound (I) or a Pharmaceutically Acceptable Salt Thereof on the Learned Helplessness Model of Depression in Rats This test is an animal model of depression based on the hypothesis that the phenomenon in which a rat does not exhibit an escape reaction, despite under escapable conditions in the same apparatus, when given a nociceptive stimulus (electric shock and the like) in an inescapable situation (a state lacking volition in the animal resulting from learned helplessness in coping with the situation) is associated with the lassitude and lack of volition observed in human depressive disorders (Drug Dev. Res., 29, p.48 (1993)). From the effects of existing antidepressants and the like on this system, this test is deemed a higher level animal model in rodents.

The male SD rats (190 to 260 g; Charles River Japan Inc.) were used in this study. On Day 1 of experiment, a partition board was placed in the center of the shuttle box to create two compartments so that the animals could not move from one compartment to another (220×200×260 mm). In each compartment, one rat was placed. The animals were retained in the shuttle box for 50 minutes and exposed to electrical shocks (IES) given via stainless floor grids with the light on. The IES was performed at an intensity of 2.5 mA electric current and controlled by computer and by applying for a random duration (10 to 90 seconds) and random on-off and off-on switching so that the animals received IES for 25 minutes in total during the 50-minute test. The animals exposed to no IES were also subjected to the same procedures using 0 mA electric current.

On Day 2 of experiment, the partition board in the center of the shuttle box was removed and replaced by a hurdle 2 cm in height to create two comportments so that the animals could move from one compartment to another. Two sessions of FR1 and FR2 were sequentially performed. Animal's behavior was evaluated according to the following procedures.

FR1: A buzzer was activated for 10 seconds. During the last 5 seconds, electric stimuli (0.5 mA) were applied to a rat via the floor grids in the compartment where the animal stayed. If the rat avoided the stimuli or moved to the other compartment to escape from the stimuli while the buzzer was sounding (between-rooms movements), the animal was given an interval of 10 seconds after the escape behavior (interval time). If the rat did not move to the other compartment, the animal was given an interval of 10 seconds after the end of buzzer (i.e., electric stimuli). This procedure counted as one trial, and was continuously repeated 15 times.

FR2: Electric stimuli (0.5 mA) were applied for 10 seconds to a rat via the floor grids in the compartment where the animal stayed. If the rat moved to the other compartment to escape from the stimuli, the animal was given an interval of 0.5 seconds after the escape behavior. If the rat did not move to the other compartment, the animal was given an interval of 0.5 seconds after the end of electric stimulation. After the interval of 0.5 seconds, electric stimuli (0.5 mA) were further applied for 10 seconds to the animal via the floor grids in the compartment where the animal stayed. If the rat moved to the other compartment to escape from the stimuli, the animal was given an interval of 15 seconds after the escape behavior. If the rat did not move to the other compartment, the animal was given an interval of 15 seconds after the end of electric stimulation. This procedure counted as one trial, and was continuously repeated 15 times.

Escape success was defined that two escape latencies in one trial in FR2 were both less than 10 seconds. The escape rate (escape response %) was calculated by the following equation to evaluate escape response.

$$\text{Escape rate (\%)} = 100 \times \frac{\text{number of successful escape trials}}{\text{total number of trials in } FR2} \quad [\text{Equation 3}]$$

(total number of trials in FR2 = 15)

Also, the between-trials movement rate (intertrial response %) was calculated by the following equation from the total frequency of between-rooms movements during the interval time in FR1 and used as a measure of psychostimulant activity.

$$\text{Between-trials movement rate (\%)} = 100 \times \frac{\text{total number of between-rooms movements}}{\text{total number of trials in } FR1} \quad [\text{Equation 4}]$$

(total number of trials in FR1 = 15)

The test compound was used for the test in suspension in distilled water for injection (manufactured by Otsuka Pharmaceutical Co.,) containing 0.5 w/v % MC. The suspension containing the test compound was orally administered 1 hour before the FR1 session (0.5 mL per 100 g of rat body weight) (test compound dose group). For a vehicle control group, a solution [distilled water for injection (manufactured by Otsuka Pharmaceutical Co.,) containing 0.5 w/v % MC] not containing the test compound was orally administered 1 hour before the test (0.5 mL per 100 g of rat body weight).
Results Administration of the compound (IC) exhibited significant ameliorating action on the escape rate reductions by IES loading in the FR2 session (an escape rate of 88.7±6.7% was exhibited at a dose of 0.3 mg/kg).

From the above, it was considered that the compound (I) having a selective affinity for adenosine $A_{2A}$ receptors, or a pharmaceutically acceptable salt thereof, is useful in the treatment and/or prevention of depressive disorders. In particular, since an effect was evident in single-dose treatment in the above-described test, the compound (IC) was considered to exhibit its effect quickly after administration.

While compound (I) or a pharmaceutically acceptable salt thereof can be administered alone as it is, usually it is preferably provided in the form of various pharmaceutical preparations. Such pharmaceutical preparations can be used for animals and human.

The pharmaceutical preparation according to the present invention may contain, as the active ingredient, compound (I) or a pharmaceutically acceptable salt thereof either alone or as a mixture with any other therapeutic active ingredient. Furthermore, these pharmaceutical preparations are prepared by mixing the active ingredient with one or more pharmaceutically acceptable carriers (e.g., diluents, solvents, excipients, or the like), and then subjecting the mixture to any method well-known in the technical field of pharmaceutics.

As for the administration route, it is preferable to select the most effective route of administration for treatment. Examples of the administration route include oral administration, and parenteral administration, for example, such as intravenous or transdermal administration and the like.

Examples of the dosage form include tablets, injections, external preparations, and the like.

Suitable dosage forms for the oral administration, for example, tablets, can be prepared by using excipients such as lactose, disintegrators such as starch, lubricants such as magnesium stearate, or binders such as hydroxypropylcellulose, or the like.

Suitable dosage forms for the parenteral administration, for example, injections, can be prepared by using diluents or solvents such as a saline solution, a glucose solution, or a mixture of brine and glucose solution, or the like.

A dosage form suitable for external preparation is not particularly limited and, for example, ointment, cream, liniment, lotion, cataplasm, plaster, tape and the like can be included. For example, ointment, cream and the like can be produced by, for example, dissolving or mixing-dispersing the active ingredient in a base such as white petrolatum and the like.

The dose and administration frequency of compound (I) or a pharmaceutically acceptable salt thereof varies depending on administration form, age and body weight of patients, properties or severity of the symptoms to be treated and the like. For general oral administration, 0.001-1000 mg, preferably 0.05-100 mg, is administered to one adult in one to several portions a day. For parenteral administration such as intravenous administration and the like, 0.001-1000 mg, preferably 0.01-100 mg, is generally administered to one adult in one to several portions a day. For transdermal administration, an external preparation containing 0.001-10% of compound (I) or a pharmaceutically acceptable salt thereof is generally applied once to several times a day. However, these doses and administration frequencies vary depending on the aforementioned various conditions.

A combination of compound (I) or a pharmaceutically acceptable salt thereof and one or more of other pharmaceutical components can also be used as the agent of the present invention for the treatment and/or prophylaxis of a mood disorder.

Examples of other pharmaceutical component to be used in combination include tricyclic or tetracyclic antidepressants such as amitriptyline hydrochloride, imipramine hydrochloride, clomipramine hydrochloride, amoxapine, mianserin hydrochloride, maprotiline hydrochloride and the like; selective serotonin reuptake inhibitors (SSRI) such as paroxetine, fluvoxamine, fluoxetine and the like; serotonin·noradrenaline uptake inhibitors (SNRI) such as milnacipran, duloxetine, venlafaxine and the like; escitalopram or oxalate thereof; sulpiride; trazodone hydrochloride and the like.

When compound (I) or a pharmaceutically acceptable salt thereof is used in combination with the above-mentioned other pharmaceutical component, compound (I) or a pharmaceutically acceptable salt thereof and other pharmaceutical component can be administered as a single preparation or a combination of plural preparations to patients in need thereof, as long as these components can be formulated as preparations, and a combination of two or more preparations is preferred. Furthermore, when compound (I) or a pharmaceutically acceptable salt thereof and other pharmaceutical component are used or administered as a combination of plural preparations, these preparations can be used or administered simultaneously or separately at an interval.

When compound (I) or a pharmaceutically acceptable salt thereof and other pharmaceutical component are administered as a combination of plural preparations, for example, a first component (a) containing compound (I) or a pharmaceutically acceptable salt thereof, and a second component (b) containing other pharmaceutical component(s) are separately formulated, and prepared into a kit. Using the kit, each component may be administered to the same subject in the same route or in different routes simultaneously or separately at an interval.

As the kit, for example, a kit comprising contents and two or more containers (e.g., vials, bags, etc.) whose material, shape, and so on are not particularly limited as long as the containers do not cause degeneration of the components which are the contents due to external temperature or light nor cause elution of chemical components from the containers during storage, and having a form which enables the administration of the above first and second components which are the contents through separate routes (e.g., tubes, etc.) or the same route is used. Specific examples thereof include tablet kits, injection kits, and the like.

The following more specifically describes the present invention by way of Examples. It should be noted, however, that the scope of the present invention is not limited by the following Examples.

EXAMPLE 1

Tablets having the following formulations are prepared according to the conventional manner. Compound (IA) (40 g), lactose (286.8 g), and potato starch (60 g) are mixed, and then a 10% aqueous solution of hydroxypropylcellulose (120 g) is added thereto. The resulting mixture is kneaded according to the conventional manner, granulated, and dried to form granules for tableting. After adding thereto 1.2 g of magnesium stearate followed by mixing, the mixture is punched with a tableting machine having a punch measuring 8 mm in diameter (Model RT-15; Kikusui) to obtain tablets (containing 20 mg of an active ingredient per tablet).

TABLE 5

| Formulation | |
|---|---|
| compound (IA) | 20 mg |
| lactose | 143.4 mg |
| potato starch | 30 mg |
| hydroxypropylcellulose | 6 mg |
| magnesium stearate | 0.6 mg |
| | 200 mg |

EXAMPLE 2

Tablets having the following formulation are prepared in the same manner as in Example 1.

TABLE 6

| Formulation | |
|---|---|
| compound (IB) | 20 mg |
| lactose | 143.4 mg |
| potato starch | 30 mg |
| hydroxypropylcellulose | 6 mg |
| magnesium stearate | 0.6 mg |
| | 200 mg |

EXAMPLE 3

Tablets having the following formulation are prepared in the same manner as in Example 1.

TABLE 7

| Formulation | |
|---|---|
| compound (IC) | 20 mg |
| lactose | 143.4 mg |
| potato starch | 30 mg |
| hydroxypropylcellulose | 6 mg |
| magnesium stearate | 0.6 mg |
| | 200 mg |

EXAMPLE 4

Injections having the following formulation are prepared according to the conventional manner. Compound (IA) (1 g) is added to distilled water for injection followed by mixing. After adjusting the pH of the mixture to 7 by adding hydrochloric acid and a sodium hydroxide aqueous solution thereto, the total volume is adjusted to 1,000 mL with distilled water for injection. The resulting mixture is aseptically charged into glass vials in 2-mL portions to obtain injections (containing 2 mg of an active ingredient per vial).

TABLE 8

| Formulation | |
|---|---|
| compound (IA) | 2 mg |
| hydrochloric acid | Appropriate amount |
| aqueous sodium hydroxide solution | Appropriate amount |
| distilled water for injection | Appropriate amount |
| | 2.00 mL |

EXAMPLE 5

In the same manner as in Example 4, an injection having the following composition is prepared.

TABLE 9

| Formulation | |
|---|---|
| compound (IB) | 2 mg |
| hydrochloric acid | Appropriate amount |
| aqueous sodium hydroxide solution | Appropriate amount |
| distilled water for injection | Appropriate amount |
| | 2.00 mL |

EXAMPLE 6

In the same manner as in Example 4, an injection having the following composition is prepared.

TABLE 10

| Formulation | |
|---|---|
| compound (IC) | 2 mg |
| hydrochloric acid | Appropriate amount |

TABLE 10-continued

| Formulation | |
|---|---|
| aqueous sodium hydroxide solution | Appropriate amount |
| distilled water for injection | Appropriate amount |
| | 2.00 mL |

REFERENCE EXAMPLE 1

Compounds (IA)-(ID) were obtained according to the method described in WO2005/063743.

REFERENCE EXAMPLE 2

N-[4-(2-Furyl)-5-(tetrahydropyran-4-carbonyl)thiazol-2-yl]-6-vinylpyridine-3-carboxamide (compound (IE))

step 1 Methyl 6-chloronicotinate (1.51 g, 8.79 mmol) was dissolved in DMF (35 mL), vinyltributyltin (3.32 mL, 11.4 mmol), dichlorobis(tri-o-tolylphosphine)palladium (206 mg, 0.262 mmol) and lithium chloride (554 mg, 13.1 mmol) were added and the mixture was stirred at 100° C. for 2 hr. The mixture was allowed to cool to room temperature, and an aqueous potassium fluoride solution was added thereto. The mixture was filtered through Celite and the residue was washed with ethyl acetate. To the obtained filtrate was added a saturated aqueous sodium hydrogen carbonate solution, and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=70:30) to give methyl 6-vinylnicotinate (1.22 g, 85%) as a colorless transparent oil.
$^1$H NMR (CDCl$_3$, δppm): 3.95 (s, 3H), 5.63 (dd, J=1.1, 10.8 Hz, 1H), 6.35 (dd, J=1.1, 17.4 Hz, 1H), 6.87 (dd, J=10.8, 17.4 Hz, 1H), 7.40 (d, J=8.2 Hz, 1H), 8.25 (dd, J=2.1, 8.2 Hz, 1H), 9.15-9.18(m, 1H).

step 2 Methyl 6-vinylnicotinate (491 mg, 2.97 mmol) obtained above was dissolved in a 50% methanol aqueous solution (8 mL). Lithium hydroxide monohydrate (276 mg, 6.57 mmol) was added thereto and the mixture was stirred at room temperature for 1 hr. The mixture was cooled to 0° C., then 3 mol/L hydrochloric acid (3 mL) was added, and the precipitated solid was collected by filtration to give 6-vinylnicotinic acid (309 mg, 70%) as a white solid.
$^1$H NMR (DMSO-d$_6$, δppm): 5.61 (dd, J=1.5, 10.8 Hz, 1H), 6.37 (dd, J=1.5, 17.4 Hz, 1H), 6.89 (dd, J=10.8, 17.4 Hz, 1H), 7.62 (d, J=8.2 Hz, 1H), 8.22 (dd, J=2.2, 8.2 Hz, 1H), 9.01 (d, J=2.2 Hz, 1H), 13.35 (brs, 1H).

step 3 2-Amino-4-(2-furyl)thiazol-5-yl=tetrahydropyran-4-yl=ketone (301 mg, 1.08 mmol) described in WO2005/063743 was dissolved in DMF (1.5 mL), EDC hydrochloride (412 mg, 2.15 mmol), DMAP (66 mg, 0.54 mmol) and 6-vinylnicotinic acid (306 mg, 1.65 mmol) were added thereto, and the mixture was stirred at 50° C. for 5 hr. The mixture was allowed to cool to room temperature, water and a saturated aqueous sodium hydrogen carbonate solution were added thereto and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=50:50), and recrystallized from ethanol-water to give compound (IE) (1.22 g, 85%) as white crystals.

$^1$H NMR (CDCl$_3$, δppm): 1.80-2.01 (m, 4H), 3.11-3.25 (m, 1H), 3.51 (ddd, J=3.1, 11.4, 11.4 Hz, 2H), 4.02-4.11 (m, 2H), 5.71 (dd, J=0.8, 10.7 Hz, 1H), 6.43 (dd, J=0.8, 17.5 Hz, 1H), 6.57 (dd, J=1.7, 3.8 Hz, 1H), 6.90 (dd, J=10.7, 17.5 Hz, 1H), 7.51 (d, J=8.2 Hz, 1H), 7.58 (dd, J=0.5, 1.7 Hz, 1H), 7.84 (d, J=3.8 Hz, 1H), 8.21 (dd, J=2.4, 8.2 Hz, 1H), 9.13 (d, J=2.4 Hz, 1H), 9.84 (brs, 1H). ESIMS m/z: [M+H]$^+$410.

REFERENCE EXAMPLE 3

N-[4-(2-Furyl)-5-(tetrahydropyran-4-carbonyl)thiazol-2-yl]-2-(pyridin-3-yl)acetamide (compound (IF))

2-Amino-4-(2-furyl)thiazol-5-yl=tetrahydropyran-4-yl=ketone (105 mg, 0.377 mmol) described in WO2005/063743 was dissolved in DMF (2.0 mL), EDC hydrochloride (421 mg, 2.20 mmol), HOBt monohydrate (340 mg, 2.21 mmol) and 3-pyridylacetic acid hydrochloride (370 mg, 2.14 mmol) were added thereto, and the mixture was stirred at 80° C. overnight. The mixture was allowed to cool to room temperature, and water and a saturated aqueous sodium hydrogen carbonate solution were added thereto. The precipitated solid was collected by filtration, and dried under reduced pressure. The obtained solid was purified by silica gel column chromatography (hexane:ethyl acetate=50:50), and recrystallized from ethanol-water to give compound (IF) (112 mg, 75%) as white crystals. $^1$H NMR (CDCl$_3$, δppm): 1.80-2.01 (m, 4H), 3.05-3.16 (m, 1H), 3.45 (ddd, J=2.8, 11.4, 11.4 Hz, 2H), 3.81 (s, 2H), 3.97-4.06 (m, 2H), 6.54 (dd, J=1.8, 3.6 Hz, 1H), 7.32 (dd, J=7.8, 4.8 Hz, 1H), 7.52-7.54 (m, 1H), 7.62-7.68 (m, 2H), 8.55-8.64 (m, 2H), 9.21 (s, 1H). APCIMS m/z: [M+H]$^+$ 398.

REFERENCE EXAMPLE 4

N-[4-(2-Furyl)-5-(tetrahydropyran-4-carbonyl)thiazol-2-yl]-1H-pyrrole-2-carboxamide (compound (IG))

In the same manner as in Reference Example 3, compound (IG) (86.0 mg, 65%) was obtained as pale-brown crystals from 2-amino-4-(2-furyl)thiazol-5-yl=tetrahydropyran-4-yl=ketone (100 mg, 0.360 mmol) described in WO2005/063743 and pyrrole-2-carboxylic acid (240 mg, 2.18 mmol).

$^1$H NMR (CDCl$_3$, δppm): 1.80-2.01(m, 4H), 3.08-3.24 (m, 1H), 3.47 (ddd, J=2.7, 11.5, 11.5 Hz, 2H), 4.00-4.09 (m, 2H), 6.34-6.36 (m, 1H), 6.56 (dd, J=1.8, 3.6 Hz, 1H), 6.86-6.88 (m, 1H), 7.06-7.10 (m, 1H), 7.55-7.57 (m, 1H), 7.71 (dd, J=0.7, 3.7 Hz, 1H), 9.49 (brs, 1H), 9.65 (brs, 1H). APCIMS m/z: [M+H]$^+$372.

REFERENCE EXAMPLE 5

N-[4-(2-Furyl)-5-(tetrahydropyran-4-carbonyl)thiazol-2-yl]-1H-indole-4-carboxamide (compound (IH))

In the same manner as in Reference Example 3, compound (IH) (97.6 mg, 63%) was obtained as milky white crystals from 2-amino-4-(2-furyl)thiazol-5-yl=tetrahydropyran-4-yl=ketone (102 mg, 0.367 mmol) described in WO2005/063743 and indole-4-carboxylic acid (331 mg, 2.05 mmol).

$^1$H NMR (CDCl$_3$, δppm): 1.80-2.01 (m, 4H), 3.17-3.28 (m, 1H), 3.50 (ddd, J=3.0, 11.2, 11.2 Hz, 2H), 4.02-4.11 (m, 2H), 6.58 (dd, J=1.7, 3.5 Hz, 1H), 7.23-7.36 (m, 2H), 7.43-7.48 (m, 1H), 7.58-7.60 (m, 1H), 7.67 (dd, J=4.2, 7.7 Hz, 2H), 7.76 (dd, J=0.7, 3.5 Hz, 1H), 8.46 (brs, 1H), 9.70 (brs, 1H). APCIMS m/z: [M+H]$^+$422.

REFERENCE EXAMPLE 6

N-[4-(2-Furyl)-5-(tetrahydropyran-4-carbonyl)thiazol-2-yl]-2-(morpholin-4-ylmethyl)pyridine-4-carboxamide (compound (II))

step 1 2-Amino-4-(2-furyl)thiazol-5-yl=tetrahydropyran-4-yl=ketone (2.00 g, 7.19 mmol) described in WO2005/063743 was dissolved in DMF (35 mL), EDC hydrochloride (5.50 g, 28.6 mmol), HOBt monohydrate (4.40 g, 28.8 mmol) and 2-(chloromethyl)isonicotinic acid (4.93 g, 28.7 mmol) obtained by the method described in WO03/043636 were added thereto, and the mixture was stirred at 80° C. overnight. The mixture was allowed to cool to room temperature, and water and a saturated aqueous sodium hydrogen carbonate solution were added thereto. The precipitated solid was collected by filtration, and dried under reduced pressure. The obtained solid was purified by silica gel column chromatography (hexane:ethyl acetate=50:50) to give 2-(chloromethyl)-N-[4-(2-furyl)-5-(tetrahydropyran-4-carbonyl)thiazol-2-yl]pyridine-4-carboxamide (700 mg, 23%) as a pale-brown solid.

$^1$H NMR (CDCl$_3$, δppm): 1.84-1.97 (m, 4H), 3.12-3.23 (m, 1H), 3.46-3.57 (m, 2H), 4.02-4.11 (m, 2H), 4.75 (s, 2H), 6.52 (dd, J=3.6, 1.7 Hz, 1H), 7.50 (dd, J=1.7, 0.7 Hz, 1H), 7.70 (dd, J=5.1, 1.7 Hz, 1H), 7.79 (dd, J=3.6, 0.7 Hz, 1H), 7.92-7.95 (m, 1H), 8.79 (dd, J=5.1, 0.7 Hz, 1H).

step 2 2-(Chloromethyl)-N-[4-(2-furyl)-5-(tetrahydropyran-4-carbonyl)thiazol-2-yl]pyridine-4-carboxamide (70.0 mg, 0.162 mmol) obtained in step 1 was dissolved in acetonitrile (2.0 mL), then morpholine (70.0 μL, 2.15 mmol) was added thereto, and the mixture was stirred with heating under reflux for 1 hr. The mixture was allowed to cool to room temperature, water and a saturated aqueous sodium hydrogen carbonate solution were added thereto. The mixture was extracted with ethyl acetate, and the organic layer was washed with saturated brine, dried over anhydrous magnesium sulfate, and concentrated under reduced pressure. The obtained residue was purified by silica gel column chromatography (chloroform:methanol=95:5), and reslurried with hexane-ethyl acetate to give compound (II) (54.6 mg, 71%) as a pale-brown solid.

$^1$H NMR (CDCl$_3$, δppm): 1.80-2.01 (m, 4H), 2.51-2.59 (m, 4H), 3.10-3.24 (m, 1H), 3.51 (ddd, J=3.0, 11.3, 11.3 Hz, 2H), 3.75-3.82 (m, 6H), 4.01-4.13 (m, 2H), 6.59 (dd, J=1.8, 3.6 Hz, 1H), 7.60 (dd, J=0.7, 1.8 Hz, 1H), 7.69 (dd, J=1.8, 5.1 Hz, 1H), 7.84 (dd, J=0.7, 3.6 Hz, 1H), 7.93-7.95 (m, 1H), 8.82 (dd, J=0.7, 5.1 Hz, 1H). ESIMS m/z: [M+H]$^+$483.

REFERENCE EXAMPLE 7

N-[4-(2-Furyl)-5-(tetrahydropyran-4-carbonyl)thiazol-2-yl]-2-methoxymethylpyridine-4-carboxamide (compound (IJ))

Under ice-cooling, 60% sodium hydride (10.0 mg, 0.250 mmol) was dissolved in DMF (1.0 mL), methanol (110 μL, 2.72 mmol) was slowly added dropwise thereto, and the mixture was stirred at 0° C. for 10 min. Then, 2-(chloromethyl)-N-[4-(2-furyl)-5-(tetrahydropyran-4-carbonyl)thiazol-2-yl]pyridine-4-carboxamide (81.0 mg, 0.189 mmol) obtained in step 1 of Reference Example 6, which was dissolved in DMF (1.0 mL), was slowly added dropwise thereto, and the mixture was stirred at room temperature for 5 hr. To the mixture were added water and a saturated aqueous sodium hydrogen carbonate solution, and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=50:50), and recrystallized from ethanol-water to give compound (IJ) (45.0 mg, 56%) as white crystals.

$^1$H NMR (CDCl$_3$, δppm): 1.80-2.01 (m, 4H), 3.14-3.23 (m, 1H), 3.52 (ddd, J=3.0, 11.2, 11.2 Hz, 2H), 3.53 (s, 3H), 4.02-4.18 (m, 2H), 4.65 (s, 2H), 6.52 (dd, J=1.8, 3.6 Hz, 1H), 7.50 (d, J=1.1 Hz, 1H), 7.71 (dd, J=1.3, 5.1 Hz, 1H), 7.79 (d, J=3.6 Hz, 1H), 7.85 (s, 1H), 8.77 (d, J=5.1 Hz, 1H), 10.41 (brs, 1H). APCIMS m/z: [M+H]$^+$428.

REFERENCE EXAMPLE 8

2-Ethoxymethyl-N-[4-(2-furyl)-5-(tetrahydropyran-4-carbonyl)thiazol-2-yl]pyridine-4-carboxamide (compound (IK))

In the same manner as in Reference Example 7, compound (IK) (47.0 mg, 57%) was obtained as white crystals from 2-(chloromethyl)-N-[4-(2-furyl)-5-(tetrahydropyran-4-carbonyl)thiazol-2-yl]pyridine-4-carboxamide (80.0 mg, 0.185 mmol) and ethanol (200 μL, 3.54 mmol).

$^1$H NMR (CDCl$_3$, δppm): 1.36 (t, J=7.1 Hz, 3H), 1.80-2.01 (m, 4H), 3.11-3.28 (m, 1H), 3.51 (ddd, J=3.2, 11.4, 11.4 Hz, 2H), 3.72 (q, J=7.1 Hz, 2H), 4.00-4.12 (m, 2H), 4.73 (s, 2H), 6.58 (dd, J=1.7, 3.6 Hz, 1H), 7.58 (dd, J=0.7, 1.7 Hz, 1H), 7.72 (dd, J=1.7, 5.0Hz, 1H), 7.84 (dd, J=0.7, 3.6 Hz, 1H), 7.92 (dd, J=0.7, 1.7Hz, 1H), 8.80 (d, J=5.0 Hz, 1H), 9.95 (brs, 1H). APCIMS m/z: [M+H]$^+$442.

REFERENCE EXAMPLE 9

N-[4-(2-Furyl)-5-(tetrahydropyran-4-carbonyl)thiazol-2-yl]-2-isopropoxymethylpyridine-4-carboxamide (compound (IL))

In the same manner as in Reference Example 7, compound (IL) (30.2 mg, 36%) was obtained as white crystals from 2-(chloromethyl)-N-[4-(2-furyl)-5-(tetrahydropyran-4-carbonyl)thiazol-2-yl]pyridine-4-carboxamide (80.1 mg, 0.185 mmol) and 2-propanol (350 μL, 4.60 mmol).

$^1$H NMR (CDCl$_3$, δppm): 1.31 (d, J=6.0 Hz, 6H), 1.80-2.01 (m, 4H), 3.15-3.22 (m, 1H), 3.51 (ddd, J=2.8, 11.4, 11.4 Hz, 2H), 3.78-3.86 (qq, J=6.0, 6.0 Hz, 1H), 4.01-4.11 (m, 2H), 4.73 (s, 2H), 6.58 (dd, J=1.8, 3.6 Hz, 1H), 7.59 (dd, J=0.6, 1.8 Hz, 1H), 7.71 (dd, J=1.5, 5.1 Hz, 1H), 7.85 (dd, J=0.4, 3.5 Hz, 1H), 7.93 (d, J=0.6 Hz, 1H), 8.79 (dd, J=0.4, 5.1 Hz, 1H), 9.91 (brs, 1H). APCIMS m/z: [M+H]$^+$456.

REFERENCE EXAMPLE 10

N-[4-(2-Furyl)-5-(tetrahydropyran-4-carbonyl)thiazol-2-yl]furo[2,3-b]pyridine-5-carboxamide (compound (IM))

2-Amino-4-(2-furyl)thiazol-5-yl=tetrahydropyran-4-yl=ketone (125 mg, 0.450 mmol) described in WO2005/063743 was dissolved in DMF (2.2 mL), EDC hydrochloride (173 mg, 0.900 mmol), HOBt monohydrate (138 mg, 0.900 mmol) and furo[2,3-b]pyridine-5-carboxylic acid (147 mg, 0.900 mmol) obtained in the method described in Tetrahedron Letters, vol. 35, p.9355 (1994) were added thereto, and the mixture was stirred at 50° C. for 2 hr, then at 70° C. for 1 hr. To the mixture were added EDC hydrochloride (173 mg, 0.900 mmol), HOBt monohydrate (138 mg, 0.900 mmol) and furo[2,3-b]pyridine-5-carboxylic acid (147 mg, 0.900 mmol), and the mixture was stirred at 70° C. for 1.5 hr. The mixture was added to water—a saturated aqueous sodium hydrogen carbonate solution (1:1) and the precipitated solid was collected by filtration and dried. The obtained solid was purified by silica gel column chromatography (hexane:ethyl acetate=50:50), and recrystallized from ethanol-water to give compound (IM) (81.2 mg, 43%).

$^1$H NMR (DMSO-d$_6$, δppm): 1.56-1.77 (m, 4H), 3.16-3.26 (m, 1H), 3.37-3.47 (m, 2H), 3.87-3.92 (m, 2H), 6.71 (dd, J=1.9, 3.5 Hz, 1H), 7.21 (d, J=2.4 Hz, 1H), 7.45 (dd, J=0.9, 3.5 Hz, 1H), 7.91 (dd, J=0.9, 1.9 Hz, 1H), 8.27 (d, J=2.4 Hz, 1H), 8.86 (d, J=2.4 Hz, 1H), 9.04 (d, J=2.4 Hz, 1H). ESIMS m/z: [M+H]$^+$424.

REFERENCE EXAMPLE 11

N-[4-(2-Furyl)-5-(tetrahydropyran-4-carbonyl)thiazol-2-yl]-2-(pyridin-2-yl)acetamide (compound (IN))

In the same manner as in step 3 of Reference Example 2, compound (IN) (125 mg, 58%) was obtained as white crystals from 2-amino-4-(2-furyl)thiazol-5-yl=tetrahydropyran-4-yl=ketone (154 mg, 0.553 mmol) described in WO2005/063743 and 2-pyridylacetic acid hydrochloride (196 mg, 1.13 mmol).

$^1$H NMR (CDCl$_3$, δppm): 1.78-1.95 (m, 4H), 3.01-3.21 (m, 1H), 3.47 (ddd, J=2.6, 11.4, 11.4 Hz, 2H), 3.98-4.09 (m, 2H), 4.03 (s, 2H), 6.57 (dd, J=1.8, 3.6 Hz, 1H), 7.25-7.34 (m, 2H), 7.59 (dd, J=0.7, 1.8 Hz, 1H), 7.70 (dd, J=0.7, 3.5 Hz, 1H), 7.74 (ddd, J=1.8, 7.7, 7.7 Hz, 1H), 8.69-8.73 (m, 1H), 12.09 (brs, 1H). APCIMS m/z: [M+H]$^+$398.

REFERENCE EXAMPLE 12

N-[4-(2-Furyl)-5-(tetrahydropyran-4-carbonyl)thiazol-2-yl]-6-methoxypyridine-3-carboxamide (compound (IO))

In the same manner as in step 3 of Reference Example 2, compound (IO) (121 mg, 54%) was obtained as white crystals from 2-amino-4-(2-furyl)thiazol-5-yl=tetrahydropyran-4-yl=ketone (150 mg, 0.539 mmol) described in WO 2005/063743 and 6-methoxynicotinic acid (101 mg, 0.659 mmol).

$^1$H NMR (CDCl$_3$, δppm): 1.80-2.01 (m, 4H), 3.10-3.25 (m, 1H), 3.51 (ddd, J=2.9, 11.4, 11.4 Hz, 2H), 4.02-4.11 (m, 2H), 4.04 (s, 3H), 6.55 (dd, J=1.7, 3.5 Hz, 1H), 6.87 (d, J=8.8 Hz, 1H), 7.53-7.57 (m, 1H), 7.83 (dd, J=0.6, 3.5 Hz, 1H), 8.10 (dd, J=2.6, 8.8 Hz, 1H), 8.77 (dd, J=0.6, 2.6 Hz, 1H), 9.93 (brs, 1H). APCIMS m/z: [M+H]$^+$414.

REFERENCE EXAMPLE 13

N-[4-(2-Furyl)-5-(tetrahydropyran-4-carbonyl)thiazol-2-yl]quinoline-3-carboxamide (compound (IP))

In the same manner as in step 3 of Reference Example 2, compound (IP) (178 mg, 76%) was obtained as pale-yellow crystals from 2-amino-4-(2-furyl)thiazol-5-yl=tetrahydropyran-4-yl=ketone (151 mg, 0.543 mmol) described in WO2005/063743 and quinoline-3-carboxylic acid (142 mg, 0.820 mmol).

$^1$H NMR (CDCl$_3$, δppm): 1.80-2.01 (m, 4H), 3.15-3.25 (m, 1H), 3.52 (ddd, J=2.9, 11.4, 11.4 Hz, 2H), 4.06-4.10 (m, 2H), 6.47 (dd, J=1.7, 3.5 Hz, 1H), 7.47 (dd, J=0.7, 1.6 Hz, 1H), 7.66-7.74 (m, 2H), 7.87-7.95 (m, 2H), 8.20 (dd, J=0.9, 8.4 Hz, 1H), 8.71 (d, J=1.8 Hz, 1H), 9.43 (d, J=2.4 Hz, 1H), 10.55 (s, 1H). APCIMS m/z: [M+H]$^+$434.

REFERENCE EXAMPLE 14

N-[4-(2-Furyl)-5-(tetrahydropyran-4-carbonyl)thiazol-2-yl]-5,6-dimethylpyridine-3-carboxamide (compound (IQ))

step 1 5,6-Dimethylpyridine-3-carbonitrile (502 mg, 3.79 mmol) obtained by the method described in J. Heterocyclic Chem., vol. 24, p. 351 (1987) was suspended in 70% aqueous ethanol (4.5 mL), sodium hydroxide (444 mg, 11.1 mmol) was added thereto, and the mixture was stirred with heating under reflux for 3 hr. The mixture was ice-cooled to 0° C., and 6 mol/L hydrochloric acid (1.9 mL) was added thereto. The mixture was concentrated under reduced pressure and the obtained residue was suspended in chloroform-methanol. The inorganic salt was removed by filtration, and the obtained filtrate was concentrated under reduced pressure to give 5,6-dimethylpyridine-3-carboxylic acid (569 mg, 99%) as a pale-pink solid.

$^1$H NMR (DMSO-d$_6$, δppm): 2.23 (s, 3H), 2.39 (s, 3H), 7.83 (d, J =1.7 Hz, 1H), 8.64 (d, J=1.7 Hz, 1H).

step 2 In the same manner as in step 3 of Reference Example 2, compound (IQ) (112 mg, 49%) was obtained as white crystals from 2-amino-4-(2-furyl)thiazol-5-yl=tetrahydropyran-4-yl=ketone (151 mg, 0.550 mmol) described in WO2005/063743 and 5,6-dimethylpyridine-3-carboxylic acid (166 mg, 1.10 mmol) obtained above.

$^1$H NMR (CDCl$_3$, δppm): 1.80-2.01 (m, 4H), 2.34 (s, 3H), 2.59 (s, 3H), 3.12-3.23 (m, 1H), 3.51 (ddd, J=2.9, 11.3, 11.3 Hz, 2H), 4.04-4.09 (m, 2H), 6.49 (dd, J=2.0, 3.6 Hz, 1H), 7.47 (d, J =1.7 Hz, 1H), 7.79 (dd, J=0.5, 3.5 Hz, 1H), 7.89 (d, J=1.7 Hz, 1H), 8.86 (d, J=2.0 Hz, 1H). ESIMS m/z: [M+H]$^+$412.

REFERENCE EXAMPLE 15

5-Ethyl-N-[4-(2-furyl)-5-(tetrahydropyran-4-carbonyl)thiazol-2-yl]pyridine-3-carboxamide (compound. (IR))

In the same manner as in step 3 of Reference Example 2, compound (IR) (145 mg, 65%) was obtained as white crystals from 2-amino-4-(2-furyl)thiazol-5-yl=tetrahydropyran-4-yl=ketone (151 mg, 0.543 mmol) described in WO2005/063743 and 5-ethylnicotinic acid (128 mg, 0.814 mmol).

$^1$H NMR (CDCl$_3$, δppm): 1.32 (t, J=7.6 Hz, 3H), 1.83-2.01 (m, 4H), 2.77 (q, J=7.6 Hz, 2H), 3.11-3.26 (m, 1H), 3.51 (ddd, J =2.9, 11.4, 11.4 Hz, 2H), 4.01-4.11 (m, 2H), 6.54 (dd, J=1.8, 3.6 Hz, 1H), 7.51-7.53 (m, 1H), 7.80 (dd, J=0.7, 3.6 Hz, 1H), 8.03-8.06 (m, 1H), 8.70 (d, J=2.0 Hz, 1H), 8.99 (d, J=2.0 Hz, 1H), 10.24 (brs, 1H). ESIMS m/z: [M+H]$^+$412.

REFERENCE EXAMPLE 16

N-[4-(2-Furyl)-5-(tetrahydropyran-4-carbonyl)thiazol-2-yl]-7,8-dihydro-5H-pyrano[4,3-b]pyridine-3-carboxamide (compound (IS))

step 1 Sodium hydride (2.06 g, 51.5 mmol) was suspended in diethyl ether (40 mL), and methanol (2.1 mL, 51.8 mmol) was added slowly at −5° C. thereto. To the mixture was added ethanol (6 mL), and the mixture was stirred at room temperature for 5 min, and cooled to 0° C. A mixture of tetrahydro- 4H-pyran-4-one (4.61 mL, 49.9 mmol) and ethyl formate (4.11 mL, 51.1 mmol) was slowly added thereto. The mixture was stirred at room temperature for 2 hr, and the resultant product was extracted with water (30 mL) (aqueous solution A).

Then, an aqueous piperidine—acetic acid solution prepared by dissolving acetic acid (1.5 mL) in water (3.5 mL) and adding piperidine (2.6 ml) thereto, and 2-cyanoacetamide (4.62 g, 54.9 mmol) were added to the above-mentioned aqueous solution A, and the mixture was stirred with heating under reflux for 4 hr. To the mixture was added acetic acid (3.6 mL) and, after cooling 0° C., the precipitated solid was collected by filtration to give 2-oxo-1,5,7,8-tetrahydro-2H-pyrano[4,3-b]pyridine-3-carbonitrile (1.72 g, 20%) as a white solid.

$^1$H NMR (CDCl$_3$, δppm): 2.89 (t, J=5.6 Hz, 2H), 3.99 (t, J=5.6 Hz, 2H), 4.54 (s, 2H), 7.59 (s, 1H). APCIMS m/z: [M−H]$^-$175.

step 2 2-Oxo-1,5,7,8-tetrahydro-2H-pyrano[4,3-b]pyridine-3-carbonitrile (2.50 g, 14.4 mmol) obtained in step 1 was dissolved in phosphoryl chloride (20 mL), and the mixture was stirred with heating under reflux for 4 hr. The mixture was allowed to cool to room temperature, and slowly added to a saturated aqueous sodium hydrogen carbonate solution at 0° C., then the mixture was extracted with chloroform. The organic layer was washed with saturated brine, dried over anhydrous magnesium sulfate, and concentrated under reduced pressure. The obtained residue was purified by silica gel column chromatography (hexane:ethyl acetate=50:50) to give 2-chloro-7,8-dihydro-5H-pyrano[4,3-b]pyridine-3-carbonitrile (1.85 g, 66%) as a white solid.

$^1$H NMR (CDCl$_3$, δppm): 3.07 (t, J=5.8 Hz, 2H), 4.07 (t, J=5.8 Hz, 2H), 4.75-4.76 (m, 2H), 7.63 (s, 1H).

step 3 2-Chloro-7,8-dihydro-5H-pyrano[4,3-b]pyridine-3-carbonitrile (1.77 g, 9.09 mmol) obtained in step 2 was dissolved in ethanol (30 mL), acetic acid (9 mL) and zinc (2.60 g) were added thereto, and the mixture was stirred with heating under reflux for 4 hr. The mixture was allowed to cool to room temperature, then filtered through Celite, and the filtrate was concentrated under reduced pressure. To the obtained residue was added a saturated aqueous sodium hydrogen carbonate solution and the mixture was extracted with chloroform. The organic layer was washed with saturated brine, dried over anhydrous magnesium sulfate, and concentrated under reduced pressure. The obtained residue was purified by silica gel column chromatography (hexane:ethyl acetate=50:50) to give 7,8-dihydro-5H-pyrano[4,3-b]pyridine-3-carbonitrile (1.06 g, 73%) as a white solid.

$^1$H NMR (CDCl$_3$, δppm): 3.10 (t, J=5.8 Hz, 2H), 4.10 (t, J=5.8 Hz, 2H), 4.79 (s, 2H), 7.59 (d, J=1.7 Hz, 1H), 8.71 (d, J=1.7 Hz, 1H). APCIMS m/z: [M+H]$^+$161.

step 4 In the same manner as in step 1 of Reference Example 14, 7,8-dihydro-5H-pyrano[4,3-b]pyridine-3-carboxylic acid (318 mg, 47%) was obtained as a white solid from 7,8-dihydro-5H -pyrano[4,3-b]pyridine-3-carbonitrile (609 mg, 3.80 mmol) obtained above.

$^1$H NMR (DMSO-d$_6$, δppm): 2.86 (t, J=5.8 Hz, 2H), 3.95 (t, J=5.8 Hz, 2H), 4.70 (s, 2H), 7.80 (d, J=1.7 Hz, 1H), 8.76 (d, J =1.7 Hz, 1H). ESIMS m/z: [M−H]$^-$178.

step 5 In the same manner as in step 3 of Reference Example 2, compound (IS) (178 mg, 74%) was obtained as white crystals from 2-amino-4-(2-furyl)thiazol-5-yl=tetrahydropyran-4-yl=ketone (152 mg, 0.546 mmol) described in WO20054063743 and 7,8-dihydro-5H-pyrano[4,3-b]pyridine-3-carboxylic acid (432 mg, 2.00 mmol) obtained above.

$^1$H NMR (CDCl$_3$, δppm): 1.80-2.01 (m, 4H), 3.10 (t, J=5.6 Hz, 2H), 3.13-3.24 (m, 1H), 3.51 (ddd, J=2.8, 11.4, 11.4 Hz, 2H), 4.03-4.14 (m, 4H), 4.79 (s, 2H), 6.50 (dd, J=1.7, 3.6 Hz, 1H), 7.46 (dd, J=0.6, 1.7 Hz, 1H), 7.78 (dd, J=0.6, 3.6 Hz, 1H), 7.82 (d, J=2.2 Hz, 1H), 8.94 (d, J=2.2 Hz, 1H), 10.58 (s, 1H). ESIMS m/z: [M+H]$^+$440.

REFERENCE EXAMPLE 17

N-[4-(2-Furyl)-5-(tetrahydropyran-4-carbonyl)thiazol-2-yl]-6,7-dihydro-5H-cyclopenta[b]pyridine-3-carboxamide (compound (IT))

step 1 6,7-Dihydro-5H-cyclopenta[b]pyridine-3-carbonitrile (901 mg, 6.25 mmol) obtained by the method described in J. Heterocyclic Chem., vol. 24, p. 351 (1987) was suspended in 6 mol/L hydrochloric acid (9 mL), and the mixture was stirred with heating under reflux for 5 hr. The mixture was ice-cooled to 0° C., and the precipitated solid was collected by filtration to give 6,7-dihydro-5H-cyclopenta[b]pyridine-3-carboxylic acid hydrochloride (543 mg, 44%) as a pale-brown solid.

$^1$H NMR (DMSO-d$_6$, δppm): 2.16 (tt, J=7.4, 7.8 Hz, 2H), 3.02 (t, J=7.4 Hz, 2H), 3.10 (t, J=7.8 Hz, 2H), 8.34 (s, 1H), 8.92 (s, 1H).

step 2 In the same manner as in step 3 of Reference Example 2, compound (IT) (134 mg, 58%) was obtained as white crystals from 2-amino-4-(2-furyl)thiazol-5-yl=tetrahydropyran-4-yl=ketone (152 mg, 0.546 mmol) described in WO2005/063743 and 6,7-dihydro-5H-cyclopenta[b]pyridine-3-carboxylic acid hydrochloride (165 mg, 0.827 mmol) obtained above.

$^1$H NMR (CDCl$_3$, δppm): 1.78-2.01 (m, 4H), 2.16-2.28 (m, 2H), 3.01 (t, J=7.6 Hz, 2H), 3.10 (t, J=7.7 Hz, 2H), 3.11-3.25 (m, 1H), 3.51 (ddd, J=3.0, 11.4, 11.4 Hz, 2H), 4.00-4.10 (m, 2H), 6.52 (dd, J=1.8, 3.6 Hz, 1H), 7.51 (dd, J=0.7, 1.7 Hz, 1H), 7.80 (dd, J=0.7, 3.6 Hz, 1H), 7.95-8.00 (m, 1H), 8.87-8.91 (m, 1H), 10.20 (brs, 1H). ESIMS m/z: [M+H]$^+$424.

REFERENCE EXAMPLE 18

N-[4-(2-Furyl)-5-(tetrahydropyran-4-carbonyl)thiazol-2-yl]-1H -indole-2-carboxamide (compound (IU))

In the same manner as in Reference Example 3, compound (IU) (97.5 mg, 63%) was obtained as pale-brown crystals from 2-amino-4-(2-furyl)thiazol-5-yl=tetrahydropyran-4-yl=ketone (102 mg, 0.366 mmol) described in WO2005/063743 and indole-2-carboxylic acid (350 mg, 2.17 mmol).

$^1$H NMR (CDCl$_3$, δppm): 1.80-2.01 (m, 4H), 3.10-3.24 (m, 1H), 3.50 (ddd, J=2.7, 11.5, 11.5 Hz, 2H), 4.01-4.11 (m, 2H), 6.59 (dd, J=1.7, 3.5 Hz, 1H), 7.14 (dd, J=0.9, 2.2 Hz, 1H), 7.19-7.25 (m, 1H), 7.36-7.43 (m, 1H), 7.46-7.52 (m, 1H), 7.60 (dd, J=0.7, 1.7 Hz, 1H), 7.72-7.77 (m, 1H), 7.83 (dd, J=0.7, 3.5 Hz, 1H), 9.21 (brs, 1H), 9.66 (brs, 1H). APCIMS m/z: [M+H]$^+$422.

REFERENCE EXAMPLE 19

6-Ethyl-N-[4-(2-furyl)-5-(tetrahydropyran-4-carbonyl)thiazol-2-yl]pyridine-3-carboxamide (compound (IV))

Compound (IE) (90.0 mg, 0.220 mmol) obtained in Reference Example 2 was dissolved in ethanol (10 mL) under an argon atmosphere, 10% palladium carbon (10%-Pd/C; containing water) (88.9 mg) was added thereto, and mixture was stirred at room temperature overnight under a hydrogen atmosphere. The mixture was filtered through Celite, and the filtrate was concentrated under reduced pressure. The obtained residue was purified by preparative thin layer chromatography (hexane:ethyl acetate=30:70), and recrystallized from ethanol-water to give compound (IV) (70.0 mg, 77%) as white crystals.

$^1$H NMR (CDCl$_3$, δppm): 1.36 (t, J=7.6 Hz, 3H), 1.80-2.01 (m, 4H), 2.94 (q, J=7.6 Hz, 2H), 3.11-3.27 (m, 1H), 3.51 (ddd, J=3.0, 11.3, 11.3 Hz, 2H), 3.99-4.13 (m, 2H), 6.54 (dd, J=1.7, 3.5 Hz, 1H), 7.35 (d, J=8.1 Hz, 1H), 7.52 (dd, J=0.7, 1.7 Hz, 1H), 7.81 (dd, J=0.7, 3.6 Hz, 1H), 8.15 (dd, J=2.2, 8.2 Hz, 1H), 9.08 (d, J=2.2 Hz, 1H), 10.13 (brs, 1H). ESIMS m/z: [M+H]$^+$412.

REFERENCE EXAMPLE 20

N-[4-(2-Furyl)-5-(tetrahydropyran-4-carbonyl)thiazol-2-yl]-6-propylpyridine-3-carboxamide (compound (IW))

step 1 In the same manner as in step 1 of Reference Example 2, methyl 6-(1-propenyl)nicotinate (327 mg, 37%) was obtained as a colorless transparent oil from methyl 6-chloronicotinate (862 mg, 6.48 mmol) and allyltributyltin (2.20 mL, 7.09 mmol). $^1$H NMR (CDCl$_3$, δppm): 1.97 (dd, J=1.7, 6.8 Hz, 3H), 3.95 (s, 3H), 6.55 (dq, J=1.7, 15.7 Hz, 1H), 6.92 (dq, J=6.8, 15.7 Hz, 1H), 7.25-7.30 (m, 1H), 8.19 (dd, J=2.2, 8.2 Hz, 1H), 9.11 (dd, J=0.5, 2.2 Hz, 1H).

step 2 In the same manner as in step 2 of Reference Example 2, 6-(1-propenyl)nicotinic acid (251 mg, 84%) was obtained as milk-white crystals from methyl 6-(1-propenyl)nicotinate (326 mg, 1.84 mmol) obtained above.

$^1$H NMR (DMSO-d$_6$, δppm): 1.91 (dd, J=1.8, 6.8 Hz, 3H), 6.58 (dq, J=1.8, 15.5 Hz, 1H), 6.91 (dq, J=6.8, 15.5 Hz, 1H), 7.48 (dd, J=0.5, 8.3 Hz, 1H), 8.15 (dd, J=2.2, 8.3 Hz, 1H), 8.95 (dd, J=0.5, 2.2 Hz, 1H), 13.24 (brs, 1H). ESIMS m/z: [M+H]$^+$164.

step 3 In the same manner as in step 3 of Reference Example 2, N-[4-(2-furyl)-5-(tetrahydropyran-4-carbonyl)thiazol-2-yl]-6-(1-propenyl)pyridine-3-carboxamide (125 mg, 33%) was obtained as white crystals from 2-amino-4-(2-furyl)thiazol-5-yl=tetrahydropyran-4-yl=ketone (257 mg, 0.908 mmol) described in WO2005/063743 and 6-(1-propenyl)nicotinic acid (251 mg, 1.26 mmol) obtained above.

$^1$H NMR (CDCl$_3$, δppm): 1.82-1.96 (m, 4H), 2.01 (dd, J=1.4, 6.8 Hz, 3H), 3.12-3.23 (m, 1H), 3.52 (ddd, J=3.0, 11.2, 11.2 Hz, 2H), 4.02-4.11 (m, 2H), 6.54-6.62 (m, 2H), 7.00 (dd, J=6.8, 15.5 Hz, 1H), 7.37 (d, J=8.4 Hz, 1H), 7.55 (dd, J=0.8, 1.6 Hz, 1H), 7.82 (d, J=3.6 Hz, 1H), 8.15 (dd, J=2.4, 8.3 Hz, 1H), 9.08 (d, J=2.4 Hz, 1H), 10.00 (brs, 1H). ESIMS m/z: [M+H]$^+$424.

step 4 In the same manner as in Reference Example 19, the title compound (IW) (96.0 mg, 76%) was obtained as white crystals from N-[4-(2-furyl)-5-(tetrahydropyran-4-carbonyl)thiazol-2-yl]-6-(1-propenyl)pyridine-3-carboxamide (125 mg, 0.296 mmol) obtained above.

$^1$H NMR (CDCl$_3$, δppm): 1.00 (t, J=7.3 Hz, 3H), 1.75-1.97 (m, 6H), 2.88 (t, J=7.6 Hz, 2H), 3.13-3.24 (m, 1H), 3.51 (ddd, J=3.1, 11.4, 11.4 Hz, 2H), 4.02-4.11 (m, 2H), 6.55 (dd, J=1.8, 3.6 Hz, 1H), 7.33 (d, J=8.2 Hz, 1H), 7.53-7.55 (m, 1H), 7.81 (d, J=3.6 Hz, 1H), 8.15 (dd, J=2.5, 8.2 Hz, 1H), 9.09 (d, J=2.1 Hz, 1H), 10.14 (s, 1H). ESIMS m/z: [M+H]$^+$426.

REFERENCE EXAMPLE 21

N-[4-(2-Furyl)-5-(tetrahydropyran-4-carbonyl)thiazol-2-yl]-7,8-dihydro-5H-thiopyrano[4,3-b]pyridine-3-carboxamide (compound (IX))

step 1 In the same manner as in step 1 of Reference Example 16, 2-oxo-1,5,7,8-tetrahydro-5H-thiopyrano[4,3-b]pyridine-3-carbonitrile (3.06 g, 37%) was obtained as a pale-yellow solid from tetrahydro-4H-thiopyran-4-one (5.00 g, 43.0 mmol).

$^1$H NMR (CDCl$_3$, δppm): 2.93 (t, J=6.0 Hz, 2H), 3.11 (t, J=6.0 Hz, 2H), 3.58 (s, 2H), 7.67 (s, 1H), 13.4 (brs, 1H).

step 2 In the same manner as in step 2 of Reference Example 16, 2-chloro-7,8-dihydro-5H-thiopyrano[4,3-b]pyridine-3-carbonitrile (1.75 g, 58%) was obtained from 2-oxo-1,5,7,8-tetrahydro-5H-thiopyrano[4,3-b]pyridine-3-carbonitrile (2.78 g, 14.4 mmol) obtained above.

$^1$H NMR (CDCl$_3$, δppm): 3.01 (t, J=6.1 Hz, 2H), 3.27 (t, J=6.1 Hz, 2H), 3.78 (s, 2H), 7.71 (s, 1H).

step 3 In the same manner as in step 3 of Reference Example 16, 7,8-dihydro-5H-thiopyrano[4,3-b]pyridine-3-carbonitrile (804 mg, 55%) was obtained from 2-chloro-7,8-dihydro-5H-thiopyrano[4,3-b]pyridine-3-carbonitrile (1.75 g, 8.31 mmol) obtained above.

$^1$H NMR (CDCl$_3$, δppm): 3.04 (t, J=6.2 Hz, 2H), 3.30 (t, J=6.2 Hz, 2H), 3.81 (s, 2H), 7.68 (d, J=2.0 Hz, 1H), 8.69 (d, J=2.0 Hz, 1H).

step 4 In the same manner as in step 1 of Reference Example 17, 7,8-dihydro-5H-thiopyrano[4,3-b]pyridine-3-carboxylic acid hydrochloride (901 mg, 78%) was obtained from 7,8-dihydro-5H-thiopyrano[4,3-b]pyridine-3-carbonitrile (874 mg, 4.96 mmol) obtained above.

$^1$H NMR (DMSO-d$_6$, δppm): 3.01 (t, J=6.2 Hz, 2H), 3.24 (t, J=6.2 Hz, 2H), 3.96 (s, 2H), 8.27-8.36(m, 1H), 8.92 (d, J=1.8 Hz, 1H). ESIMS m/z: [M-H]$^{31}$ 194.

step 5 In the same manner as in step 3 of Reference Example 2, compound (IX) (79.0 mg, 68%) was obtained as pale-brown crystals from 2-amino-4-(2-furyl)thiazol-5-yl=tetrahydropyran-4-yl=ketone (70.7 mg, 0.254 mmol) described in WO2005/063743 and 7,8-dihydro-5H-thiopyrano[4,3-b]pyridine-3-carboxylic acid hydrochloride (90.9 mg, 0.392 mmol) obtained above.

$^1$H NMR (CDCl$_3$, δppm): 1.81-2.01 (m, 4H), 3.05 (t, J=6.2 Hz, 2H), 3.15-3.22 (m, 1H), 3.33 (t, J=6.0 Hz, 2H), 3.51 (ddd, J=2.9, 11.4, 11.4 Hz, 2H), 3.83 (s, 2H), 4.03-4.10 (m, 2H), 6.53 (dd, J=1.8, 3.5 Hz, 1H), 7.51 (dd, J=0.7, 1.8 Hz, 1H), 5 7.81 (dd, J=0.7, 3.5 Hz, 1H), 7.94-7.96 (m, 1H), 8.95 (d, J=2.2 Hz, 1H). ESIMS m/z: [M+H]$^+$456.

REFERENCE EXAMPLE 22

5-Acetyl-N-[4-(2-furyl)-5-(tetrahydropyran-4-carbonyl)thiazol-2-yl]-6-methylpyridine-3-carboxamide (compound (IY))

step 1 In the same manner as in step 2 of Reference Example 2, 5-acetyl-6-methylpyridine-3-carboxylic acid (462 mg, quantitative) was obtained as a yellow solid from ethyl 5-acetyl-6-methylpyridine-3-carboxylate (561 mg, 2.71 mmol) obtained by the method described in Synthesis, vol. 5, p.400 (1986).

$^1$H NMR (DMSO-d$_6$, δppm): 2.63 (s, 3H), 2.66 (s, 3H), 8.54 (d, J =2.0 Hz, 1H), 9.01 (d, J=2.0 Hz, 1H).

step 2 2-Amino-4-(2-furyl)thiazol-5-yl=tetrahydropyran-4-yl=ketone (71.2 mg, 0.256 mmol) described in WO2005/063743 was dissolved in DMF (0.5 mL), (benzotriazol-1- yloxy)tripyrrolidinophosphonium hexafluorophosphate (PyBOP) (262 mg, 0.510 mmol), diisopropylethylamine (DIPEA) (150 μL, 0.860 mmol) and 5-acetyl-6-methylpyridine-3-carboxylic acid (93.2 mg, 0.520 mmol) obtained above were added thereto, and the mixture was stirred at 80° C. overnight. The mixture was allowed to cool to room temperature, water and a saturated aqueous sodium hydrogen carbonate solution were added thereto and the mixture was extracted with ethyl acetate. The organic layer was washed with saturated brine, and dried over anhydrous magnesium sulfate. The solvent was evaporated under reduced pressure and the obtained residue was purified by silica gel column chromatography (hexane:ethyl acetate=50:50), and reslurried with ethanol-water to give compound (IY) (87.4 mg, 77%) as a pale-yellow solid.

$^1$H NMR (CDCl$_3$, δppm): 1.81-2.01 (m, 4H), 2.67 (s, 3H), 2.86 (s, 3H), 3.13-3.23 (m, 1H), 3.51 (ddd, J=2.9, 11.4, 11.4 Hz, 2H), 4.03-4.10 (m, 2H), 6.56 (dd, J=1.7, 3.5 Hz, 1H), 7.55 (dd, J =0.6, 1.7 Hz, 1H), 7.82 (d, J=0.6, 3.5 Hz, 1H), 8.54 (d, J =2.4 Hz, 1H), 9.11 (d, J=2.4 Hz, 1H). ESIMS m/z: [M+H]$^+$ 440.

REFERENCE EXAMPLE 23

5-Ethyl-N-[4-(3-furyl)-5-(tetrahydropyran-4-carbonyl)thiazol-2-yl]pyridine-3-carboxamide (compound (IZ))

In the same manner as in step 3 of Reference Example 2, compound (IZ) (177 mg, 79%) was obtained as white crystals from 2-amino-4-(3-furyl)thiazol-5-yl=tetrahydropyran-4-yl=ketone (151 mg, 0.541 mmol) obtained by the method described in WO2005/063743 and 5-ethylnicotinic acid (249 mg, 1.64 mmol).

$^1$H NMR (CDCl$_3$, δppm): 1.34 (t, J=7.6 Hz, 3H), 1.80-2.01 (m, 4H), 2.80 (q, J=7.6 Hz, 2H), 3.11-3.18 (m, 1H), 3.51 (ddd, J =2.8, 11.4, 11.4 Hz, 2H), 4.01-4.10 (m, 2H), 7.01 (dd, J=0.7, 1.8 Hz, 1H), 7.45-7.48 (m, 1H), 8.10-8.13 (m, 1H), 8.63 (dd, J=0.7, 1.5 Hz, 1H), 8.71-8.76 (m, 1H), 9.02-9.05 (m, 1H). ESIMS m/z: [M+H]$^+$412.

REFERENCE EXAMPLE 24

N-[4-(3-Furyl)-5-(tetrahydropyran-4-carbonyl)thiazol-2-yl]-6,7-dihydro-5H-cyclopenta[b]pyridine-3-carboxamide (compound (IAA))

In the same manner as in step 3 of Reference Example 2, compound (IAA) (71.1 mg, 39%) was obtained as white crystals from 2-amino-4-(3-furyl)thiazol-5-yl=tetrahydropyran-4-yl=ketone (120 mg, 0.432 mmol) and 6,7-dihydro-5H -cyclopenta[b]pyridine-3-carboxylic acid hydrochloride (172 mg, 0.870 mmol).

$^1$H NMR (CDCl$_3$, δppm): 1.80-2.01 (m, 4H), 2.18-2.30 (m, 2H), 3.03-3.20 (m, 5H), 3.52 (ddd, J=2.9, 11.3, 11.3 Hz, 2H), 4.01-4.10 (m, 2H), 7.03 (dd, J=0.6, 2.0 Hz, 1H), 7.48 (dd, J =1.7, 1.7 Hz, 1H), 8.08-8.10 (m, 1H), 8.68-8.70 (m, 1H), 8.95-8.97 (m, 1H). ESIMS m/z: [M+H]$^+$424.

Industrial Applicability

The present invention can be utilized for the treatment and/or prophylaxis of a mood disorder such as a depressive disorder (e.g., major depression, dysthymia, a depression-related syndrome or the like), symptom of depression due to physical disorder, drug-induced symptom of depression or the like.

The invention claimed is:

1. A method of treating a mood disorder, comprising administering to a patient an effective amount of a thiazole derivative represented by the formula (IC)

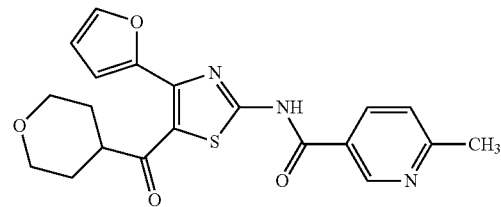

(IC)

or a pharmaceutically acceptable salt thereof, wherein the mood disorder is major depression, a depression-related syndrome, a symptom of depression due to a physical disorder or a drug-induced symptom of depression.

2. The method according to claim 1, wherein the mood disorder is a depression-related syndrome.

3. The method according to claim 1, wherein the mood disorder a symptom of depression due to a physical disorder.

4. The method according to claim 1, wherein the mood disorder is major depression.

5. The mood disorder according to claim 1, wherein the mood disorder is a drug-induced symptom of depression.

* * * * *